(12) United States Patent
Haberer et al.

(10) Patent No.: US 10,959,995 B2
(45) Date of Patent: Mar. 30, 2021

(54) METHODS OF ACUTE RESTORATION OF VASCULAR COMPLIANCE

(71) Applicant: Alumend, LLC, Sioux Falls, SD (US)

(72) Inventors: Barbara R. Haberer, Hartford, SD (US); Therese J. Downey, Brookings, SD (US); Ronald E. Utecht, Madison, SD (US)

(73) Assignee: Alumend, LLC, Sioux Falls, SD (US)

(*) Notice: Subject to any disclaimer, the term of this patent is extended or adjusted under 35 U.S.C. 154(b) by 0 days.

(21) Appl. No.: 14/777,111

(22) PCT Filed: Mar. 14, 2014

(86) PCT No.: PCT/US2014/027479
§ 371 (c)(1),
(2) Date: Sep. 15, 2015

(87) PCT Pub. No.: WO2014/152564
PCT Pub. Date: Sep. 25, 2014

(65) Prior Publication Data
US 2016/0030413 A1 Feb. 4, 2016

Related U.S. Application Data

(60) Provisional application No. 61/794,095, filed on Mar. 15, 2013.

(51) Int. Cl.
*A61K 31/473* (2006.01)
*A61K 9/00* (2006.01)
*A61K 41/00* (2020.01)
*A61N 5/06* (2006.01)
*A61K 45/06* (2006.01)

(52) U.S. Cl.
CPC .......... *A61K 31/473* (2013.01); *A61K 9/0019* (2013.01); *A61K 41/0042* (2013.01); *A61K 45/06* (2013.01); *A61N 5/062* (2013.01); *A61N 2005/0602* (2013.01)

(58) Field of Classification Search
None
See application file for complete search history.

(56) References Cited

U.S. PATENT DOCUMENTS

| 10,053,521 B2 | 8/2018 | Utecht et al. | |
| 2002/0198385 A1* | 12/2002 | Lewis | C07D 221/14 546/122 |
| 2005/0059703 A1* | 3/2005 | Wilhelm | A61K 31/00 514/338 |

FOREIGN PATENT DOCUMENTS

| WO | 2005044309 A1 | 5/2005 | |
| WO | WO 2005044309 A1 * | 5/2005 | ......... A61K 41/0042 |
| WO | WO 2014113450 A1 * | 7/2014 | ........... A61K 31/473 |

OTHER PUBLICATIONS

Harvard Men's Health Watch, Blood pressure and your brain, Oct. 2009, Harvard Health Publishing, printed from https://www.health.harvard.edu/newsletter_article/blood-pressure-and-your-brain, 6 pages (Year: 2009).*

Database Biosis [Online] Biosciences Information Service, Philadelphia, PA, US; 2004, Kloster Kaia L et al: "Use of novel crosslinking agents for post-angioplasty vascular repair and local drug delivery", abstract & FASEB Journal, vol. 18, No. 4-5, 2004, p. Abst. 384.10, FASEB Meeting on Experimental Biology: Translating the Genome; Washington, District of Columbia, Abstract only.

Kaia L. Kloster et al: "Preferential localization of varying forms of photoactive 1,8-naphthalimide compounds within the atheromatous arterial wall", Lasers in Surgery and Medicine, vol. 26, No. 3, Mar. 28, 2000 (Mar. 28, 2000), pp. 316-322.

Munger, et al., "A Novel Photochemical Cross-Linking Technology to Improve Luminal Gain, Vessel Compliance, and Buckling Post-Angioplasty in Porcine Arteries," Journal of Biomedical Materials, Feb. 2016, vol. 104B, Issue 2, pp. 375-384.

* cited by examiner

*Primary Examiner* — Gigi G Huang
(74) *Attorney, Agent, or Firm* — Burns & Levinson, LLP; Shawn P. Foley

(57) ABSTRACT

Disclosed herein is a compound for use in a composition applied to a blood vessel, wherein the compound softens and/or disrupts the crystalline matrix of calcified plaque, as well as acutely restoring the vascular compliance at the treatment site of the blood vessel, while maintaining luminal gain during angioplasty. Methods of treatment comprising applying the disclosed composition are also disclosed. Plaque-softening compounds are also disclosed.

14 Claims, 18 Drawing Sheets

METHODS OF ACUTE RESTORATION OF VASCULAR COMPLIANCE

CROSS-REFERENCE TO RELATED APPLICATIONS

This application is a U.S. national stage application under 35 U.S.C. 371 of International Application No, PCT/US2014/027479 filed on Mar. 14, 2014, which in turn claims priority to U.S. Provisional Application No. 61/794,095, filed on Mar. 15, 2013, both of which are incorporated by reference herein in their entirety for all purposes.

DESCRIPTION OF THE INVENTION

Field of the Invention

The present invention is directed to compounds that may disrupt the hard and crystalline structure of plaque. These compounds may be used in a composition to soften plaque. Methods of use of the disclosed compounds and/or compositions are also disclosed.

BACKGROUND OF THE INVENTION

Vascular plaque causes several medical conditions, including but not limited to, coronary artery disease, carotid artery disease, and peripheral artery disease.

Atherogenesis is the developmental process of atheromatous plaques. The build-up of an atheromatous plaque is a slow process, developed over a period of several years through a complex series of cellular events occurring within the arterial wall, and in response to a variety of local vascular circulating factors. Atheromatous plaques form in the arterial tunica intima, a region of the vessel wall located between the endothelium and the tunica media. The bulk of these lesions are made of excess fat, collagen, and elastin. At first, as the plaques grow, only wall thickening occurs without any significant narrowing. Stenosis is a late event, which may never occur and is often the result of repeated plaque rupture and healing responses, not just the atherosclerotic process by itself. Such vascular stenoses are alternatively referred to as vascular lesions.

Intracellular microcalcifications form within vascular smooth muscle cells of the surrounding muscular layer, specifically in the muscle cells adjacent to the atheromas. In time, as cells die, this leads to extracellular calcium deposits between the muscular wall and outer portion of the atheromatous plaques. The outer, older portions of the plaque become more calcific, less metabolically active and more physically rigid over time.

Two plaque types can be distinguished:

The fibro-lipid (fibro-fatty) plaque is characterized by an accumulation of lipid-laden cells underneath the intima of the arteries, typically without narrowing the lumen due to compensatory expansion of the bounding muscular layer of the artery wall. Beneath the endothelium there is a "fibrous cap" covering the atheromatous "core" of the plaque. The core consists of lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger "foamy" cells and capillaries. These type of plaques are sometimes referred to as vulnerable plaques, and usually produce the most damage to the individual when they rupture, often leading to fatal myocardial infarction when present within the coronary arteries.

The fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and, rarely, lipid-laden cells.

Atheromas within the vessel wall are soft and fragile with little elasticity. In addition, the calcification deposits between the outer portion of the atheroma and the muscular wall of the blood vessel, as they progress, lead to a loss of elasticity and stiffening of the blood vessel as a whole.

The calcification deposits, after they have become sufficiently advanced, are partially visible on coronary artery computed tomography or electron beam tomography (EBT) as rings of increased radiographic density, forming halos around the outer edges of the atheromatous plaques, within the artery wall. On CT, >130 units on the Hounsfield scale (some argue for 90 units) has been the radiographic density usually accepted as clearly representing tissue calcification within arteries. A carotid intima-media thickness scan (CIMT can be measured by B-mode ultrasonography) measurement has been recommended by the American Heart Association as the most useful method to identify atherosclerosis.

Intravascular ultrasound (IVUS) and optical coherence tomography (OCT) are the current most sensitive intravascular methods for detecting and measuring more advanced atheroma within living individuals. However, these imaging systems are seldom used for assessment of atheroma in view of their cost, which is not reimbursed in many medical environments, as well as invasive risks.

Angiography, since the 1960s, has been the traditional way of evaluating atheroma. However, angiography is only motion or still images of dye mixed with the blood within the arterial lumen and do not directly visualize atheroma. Rather, the wall of arteries, including atheroma with the arterial wall, generally remain invisible, with only limited shadows which define their contoured boundaries based upon x-ray absorption. The limited exception to this rule is that with very advanced atheroma, with extensive calcification within the wall, a halo-like ring of radiodensity can be seen in older patient, especially when arterial lumens are visualized end-on. On cine-floro, cardiologists and radiologists typically look for these calcification shadows to recognize arteries before they inject any contrast agent during angiograms.

Interventional vascular procedures, such as percutaneous transluminal angioplasty (PTA) for peripheral vascular disease and percutaneous transluminal coronary angioplasty (PTCA) for coronary artery disease, are typically performed using an inflatable balloon dilatation catheter to restore increased luminal diameter at the vascular lesion. During a typical PTA procedure, the dilatation catheter is positioned within the blood vessel at the location of the narrowing caused by the lesion, and the balloon is expanded with inflation fluid to dilate the vessel lumen. Following the dilatation, it is common to introduce a second balloon catheter which carries and deploys an expandable metal stent which serves to maintain vessel patency.

However, patients with calcified plaque present a much more difficult challenge for intervention. Indeed, presentation of diffuse, calcified vascular plaque within coronary arteries is often one of the most critical exclusion criteria for PTCA patient candidates, and these patients are instead required to receive invasive coronary artery bypass graft (CABG) surgery to alleviate the coronary blood flow deficiencies. On the other hand, patients presenting diffuse, calcified vascular plaque in their peripheral arteries and veins may still be eligible for PTA vascular intervention, but these patients typically require a preliminary interventional procedure involving plaque removal, such as atherectomy catheters.

In the event that an atherectomy procedure is required, the interventional physician must first deploy an embolic protection device (EPD) within the vessel being treated at a location which is distal (i.e., downstream relative to blood flow) to the atherectomy treatment site. Despite the adjunctive use of such an EPD, plaque particulates which are dislodged by the atherectomy device can occasionally escape the EPD and travel downstream within the vasculature causing a stroke, heart attack or otherwise permanently compromised distal vascular blood flow. In any event, the use of atherectomy devices produces substantial trauma to the blood vessel, and can produce serious complications such as thrombosis, as well as poor vascular healing response leading to premature restenosis.

To the extent that the interventional physician performs a PTA procedure within a blood vessel containing a lesion formed of calcified plaque, dilating such a lesion is more likely to produce increased vascular damage to the vascular tissue, such as microdissections of the vascular tissue.

Significant research efforts have been made over the past several years to better understand the complex mechanisms associated with the development of atherosclerotic vascular disease, as well as those mechanisms associated with restenosis following interventional revascularization procedures such as balloon angioplasty of target lesions within arteries, as well as the eventual onset of in-stent tissue ingrowth or restenosis (ISR) following stent implantation with certain patients.

For the past few decades, it has been generally understood that restenosis in general, as well as ISR, are largely the result of scar tissue formation provoked at the vascular treatment site during the vascular healing response, which was initiated by the traumatic, inflammatory injuries resulting from PTCA, PTA and stent implantation. While other factors, such as genetics, diet, exercise, smoking, diabetes and the like clearly constitute factors which strongly influence patient outcomes relative to interventional treatment of vascular disease, the interventional cardiovascular community has only recently begun to properly understand the complex biomechanics associated with angioplasty, stenting and restenosis.

With the advent of bare-metal stents (BMS) being implanted during arterial revascularization procedures, a significant reduction in restenosis with patients previously treating only with balloon catheter angioplasty has been obtained. In fact, it has become quite common for BMS to be implanted during catheter-based revascularization of coronary arterial disease (CAD), which is deployed during percutaneous transluminal coronary angioplasty (PTCA). Implantation of BMS has more recently also become a useful adjunct during revascularization for treatment of peripheral arterial disease (PAD), which are deployed during percutaneous transluminal angioplasty (PTA).

With the introduction of BMS implantation as an adjunct to both PTCA and PTA procedures, in order to improve patency outcomes (i.e., reduce incidence of restenosis), it has become ordinary clinical practice to place BMS patients following stent implantation on a three to four month regimen of platelet-inhibiting drugs, such as Clopidogrel (e.g., marketed by Bristol-Myers Squibb and Sanofi under the trade name PLAVIX®). Clopidogrel is an oral, thienopyridine class antiplatelet agent used to inhibit blood clot formation in critical arterial vasculature (e.e., coronary, cerebral and certain peripheral arteries). This prophylactic administration of anti-platelet-aggregating agents is given to patients receiving a stent implant in order to mitigate the risk of thrombus formation at the treatment site while the vessel is healing. During this critical healing period of approximately 90-120 days following stent implantation, the vessel will normally repopulate the treatment site with healthy endothelial cells, which will eventually cover over the struts of the metallic stent implant, thereby removing the foreign object from direct exposure to the bloodstream and potential risk of thrombus formation.

However, ISR continued to affect a significant portion of patients receiving BMS, thus requiring repeated interventions. In the case of PTCA, occasionally patient death results before re-intervention can be made. While the consequence of restenosis following PTA is certainly less severe than PTCA, it has nonetheless proven quite difficult to maintain patency of certain peripheral vasculature, due to the diffuse nature of peripheral lesions, as well as the tendency of such lesions to become moderately to severely calcified.

In response to the relatively high incidence of ISR of BMS implants, over the past 15 years drug-eluting stents (DES) have been used. DES comprise essentially a coated BMS, such that the BMS metallic platform serves as a substrate over which drug-impregnated polymer coatings are deposited. The polymer matrix contains one of several anti-proliferative agents (e.g., sirolium, everolimus, paclitaxel, etc.), which gradually are released from the polymer coating, ultimately interacting with the vascular tissue to inhibit the onset of neointimal proliferation, often characterized as neointimal hyperplasia (NH). NH is characterized by an uncontrolled proliferation of smooth muscle cell ingrowth, which ultimately produces ISR. The polymer matrix serves to provide a gradual release of the anti-proliferative agent into the tissue at the desired release kinetics of between 30-120 days, to inhibit NH while the vessel is proceeding through the most critical healing period.

Unfortunately, potentially-fatal complications have unexpectedly emerged with a portion of DES patients, known as late-stage thrombosis (LST). This late-stage formation of thrombus can occur at anytime, ranging from several weeks, to several months or even years after the implant of the DES, often causing sudden, fatal myocardial infarction (MI). Of particular concern is the fact that MI events will often occur with DES patients without any advance warning signs, such as angina or shortness of breath.

The apparent cause of LST with DES has been attributed to adverse reactions between the vascular tissue and the drug-impregnated polymer coatings used to provide the desired 30-120 day release kinetics profile required for the various anti-proliferative drugs being administered (e.g., sirolimus, everolimus, paclitaxel, etc.) Apparently, this tissue reaction directly interferes with, or disrupts, the necessary healing response associated with recruitment of healthy endothelial cells onto the surface of the implanted stent, in order to remove the exposed stent struts from the blood stream and eliminating risk of thrombus formation.

As a result, it has become necessary for DES patients to continue with their regimen of platelet anti-aggregating medication for extended periods, perhaps years or even a lifetime, in order to prevent LST. Of course, the chronic use of these platelet-inhibiting drugs is not only enormously expensive, in comparison to occasional repeated revascularizations with patients receiving only BMS implants, but these medications produce numerous undesirable medical side-effects. Additionally, patients receiving anti-platelet therapy cannot submit to even simple surgical procedures, unless they temporarily suspend their medication, in order to avoid severe bleeding. Of course, by suspending the anti-platelet medication, the DES patient is immediately at increased risk of LST. Thus, the DES dilemma is one where the effort to reduce the risk of ISR, and the need for occasional repeat angioplasty, has produced a potentially much more serious risk of LST. Of course, it is beyond debate that vascular stents, and especially coronary stents, simply cannot be explanted from the patient. So a need clearly exists to improve this approach.

Consequently, drug-eluting balloons have only recently been introduced as an alternative approach to delivery of anti-proliferative agents, such as paclitaxel, to the vascular treatment site. Unfortunately, the results to date have not been very encouraging, and it has proven quite challenging to avoid loss of the drug from the surface of the coated balloon during introduction through the vasculature to the treatment site. It has proven to be equally challenging to effectively transfer an appropriate amount of the drug from the balloon surface and onto the vessel wall. Again, a need clearly exists to improve this approach.

It is accordingly a primary object of the invention to provide a compound, in the form of a composition, to be administered to a patient in need thereof, wherein the compound will not only disrupt the crystalline structure of the calcified plaque resulting in at least one of a softening of the plaque, and an increase in lumen diameter, but will also acutely restore the vascular treatment site to more normal levels of compliance or distensibility, while retaining luminal gain.

SUMMARY OF THE INVENTION

In accordance with the invention, there is disclosed a kit of parts for use in restoring vascular compliance comprising: a composition comprising a 4-amino-1,8-naphthalimide; a delivery system for delivery of the composition into a blood vessel; and an activating agent for activating the composition after the composition has been applied to the blood vessel.

In another aspect, there is disclosed a method of restoring vascular compliance in a diseased blood vessel, comprising: inserting a delivery system into the blood vessel; applying a bolus of a composition comprising a 4-amino-1,8-naphthalimide compound to the blood vessel; activating the composition with a sufficient amount of an activating agent to restore the vascular compliance of the blood vessel.

In a further aspect, there is disclosed a method of inhibiting smooth muscle cell proliferation in a diseased blood vessel, comprising: performing an interventional procedure on the diseased blood vessel that initiates smooth muscle cell proliferation in the diseased blood vessel; and applying a bolus of a composition comprising a 4-amino-1,8-naphthalimide compound to the diseased blood vessel; wherein the application of the composition inhibits the smooth muscle cell proliferation in the diseased blood vessel.

There is disclosed a method of restoring vascular compliance of a blood vessel, comprising: performing an interventional procedure on the diseased blood vessel that initiates smooth muscle cell proliferation in the diseased blood vessel; and applying a bolus of a composition comprising a 4-amino-1,8-naphthalimide compound to the diseased blood vessel in an amount sufficient for the composition to reach an immediate area of the diseased blood vessel where the interventional procedure was performed as well as the surrounding areas; wherein the application of the composition to the immediate and surrounding areas of the interventional procedure restores the vascular compliance without exhibiting any areas of mismatched vascular compliance.

There is also disclosed a method of acutely restoring vessel compliance to a level approaching normal limits, comprising: performing a revascularization procedure on the vascular treatment site; applying a bolus of a composition comprising a 4-amino-1,8-naphthalimide compound to the vascular treatment site in an amount such that the vascular treatment site immediately re-establishes a vasomotion function to accommodate pulsatile blood flow, while retaining the luminal gain achieved during the revascularization procedure; wherein the vessel compliance of the vascular treatment site is acutely restored to a level approaching normal limits.

Further, there is disclosed a method for maintaining luminal gain of a diseased blood vessel, comprising: increasing a luminal gain of a diseased blood vessel using a dilatation device; applying a composition comprising a 4-amino-1,8-naphthalimide compound to the diseased blood vessel having an increased luminal gain; activating a composition with an activating agent to release polyether functional groups; reinforcing a wall of the diseased blood vessel with the released polyether functional groups; wherein the reinforced wall retains the luminal gain without compromising the vascular compliance of the diseased blood vessel.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIGS. 4a and b are photos of an isolated section of a blood vessel comprising a plaque matrix. FIGS. 4c-d are photos of the same blood vessel after it has been subjected to angioplasty. FIGS. 4e-f are photos of the same artery after it has been treated with a plaque-softening compound.

FIGS. 5a and b are photos of an isolated section of a blood vessel comprising a plaque matrix. FIGS. 5c-d are photos of the same blood vessel after it has been subjected to angioplasty. FIGS. 5e-f are photos of the same artery after it has been treated with a plaque-softening compound.

FIGS. 6a-c are photos of an isolated section of a blood vessel comprising a plaque matrix. FIGS. 6d-f are photos of the same blood vessel after it has been treated with a plaque-softening compound.

FIG. 7a is a photo of an isolated section of a blood vessel comprising a plaque matrix. FIGS. 7b-c are photos of the same blood vessel after it has been subjected to angioplasty. FIGS. 7d-e are photos of the same artery after it has been treated with a plaque-softening compound.

DESCRIPTION OF THE EMBODIMENTS

Figure 1:
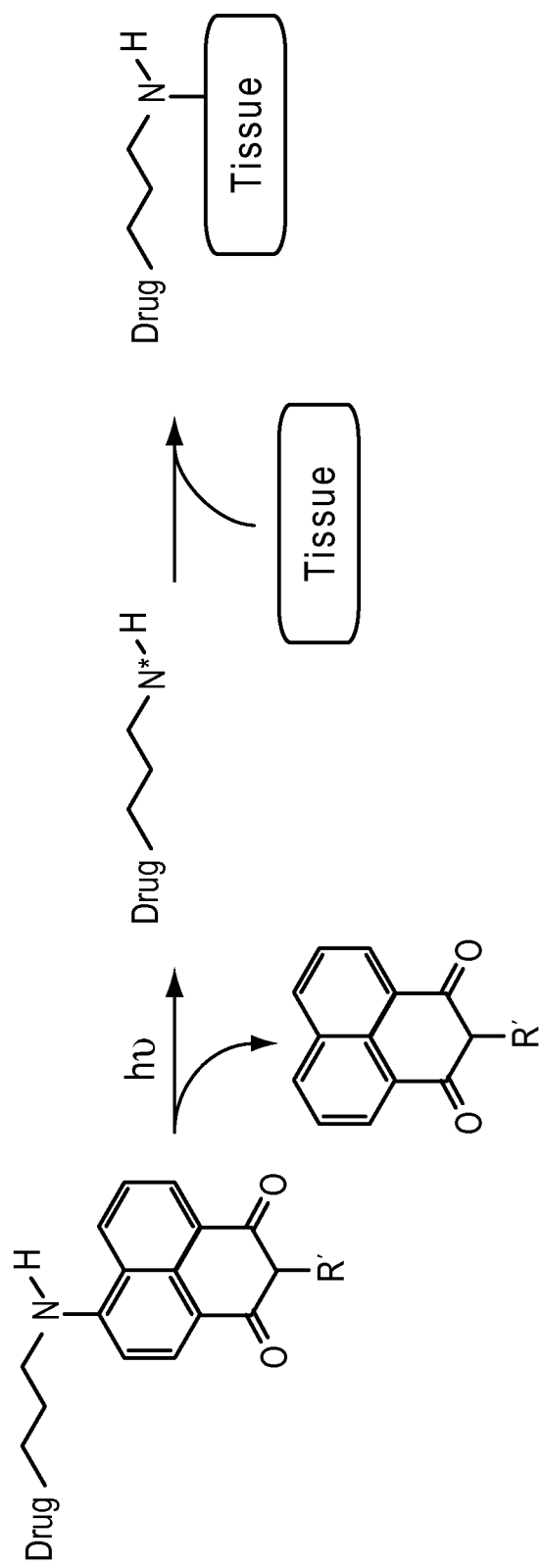
FIG. 1 illustrates an exemplary reaction scheme for tethering a pharmacological agent to a tissue, such as a blood vessel.

Reference will now be made in detail to the present embodiment(s) (exemplary embodiments) of the invention, an example(s) of which is (are) illustrated in the accompanying drawings. Wherever possible, the same reference numbers will be used throughout the drawings to refer to the same or like parts.

Over the past 5-10 years, significant insights have evolved relative to the various mechano-biological mechanisms, which are believed to exist at both molecular and cellular levels (e.g., turnover of collagen), and which manifest at tissue and organ levels. Only within the past few years, however, have these new insights been reported, observing that mechanical loads at tissue and organ levels (e.g., increased pulse pressure) are apparently sensed by molecular structure and result in altered gene expression, to the effect that the body will self-regulate its associated tissues and organs to maintain a biologically preferred state of "tensional homeostasis."

In recent medical literature, for example, relatively sophisticated mathematically-based models have been proposed to both quantify and interrelate the various mechanisms of arterial remodeling which appear to predominate operating under specific circumstances such as hypertension, which ultimately leads to vessel lumen loss (i.e., stenosis and restenosis). Humphrey J. Mechanisms of Arterial Remodeling in Hypertension: Coupled Role of Wall Shear and Intraluminal Stress. Journal of Hypertension. 2008; 52: 195-200, the disclosure of which is hereby incorporated by reference.

This article (Humphrey Paper) reports the following observations and underlying theories, which largely align with the tenet of tensional homeostasis (TH), such as the following:

a) Focal adhesions in smooth muscle cells and fibroblasts tend to increase in area in response to local increases in mechanical loading, so as to maintain the stress constant at a biologically preferred level;

b) Fibroblasts tend to increase the tractions that they exert on the extracellular matrix when external loads are decreased from a biologically preferred value;

c) Vascular smooth muscle cells tend to re-lengthen to their normal, preferred values when an arteriole is forced into a vasoconstricted state for an extended period;

d) Arteries tend to decrease in caliber (i.e., lumen size) in response to extension-induced increases in axial stress;

e) Stress fibers within endothelial and vascular smooth muscle cells appear to disassemble and then reassemble in a mechanically preferred manner when perturbed from a normal value of mechanical stress or strain; and f) Although changes in cytoskeleton and integrins occur within minutes, changes at the cell-cell and cell-matrix level occur over hours, and those at the vascular level occur over days to weeks or months.

It has been observed that the flow of blood within a vessel produces a wall shear stress (WSS) at the interface of the intima of the vascular wall, and that varying levels of WSS potentially contribute to the proliferation of neointimal proliferation and increased neointimal thickness (NT) and eventual stenosis and/or restenosis following angioplasty. Cellular mechanisms within the vasculature treatment site, such as membrane receptors, are highly sensitive to conditions of reduced vascular flow, and activate intracellular signals which promote the proliferation of neointimal tissue, leading to restenosis.

The analysis of the complex in vivo biomechanics of arterial disease (e.g., pulsatile blood flow, nonlinear anisotropic vascular wall properties, etc.) render scientific quantification of these mechano-biological mechanisms quite challenging. However, at a high level the normal human artery is subjected to three primary mechanical stresses, namely:

a) Blood-flow induced wall shear stress (WSS) $\tau_w$;

b) Blood-pressure induced circumferential wall stress $\sigma_\theta$; and c) Axial wall stress $\sigma\sigma_z$.

Axial wall stress is attributed to the contribution of elastin in the vascular wall, which appears to arise during development and to persist into maturity because of the relatively long half-life of elastin.

Based upon the foregoing, the mean values of these three components of stress (i.e., forces acting over oriented areas) can be calculated as follows:

$$\tau_w = 4\mu Q/(\pi a^3) \quad \text{(Equation 1)}$$

$$\sigma_\theta = Pa/h \quad \text{(Equation 2)}$$

$$\sigma\sigma_z = f/\pi h(2a+h) \quad \text{(Equation 3)}$$

With respect to Equations 1-3 cited above, the following parameters are defined below:

µ is the blood viscosity;
Q is the mean volumetric flow rate;
a is the luminal radius;
h is the wall thickness in any pressurized configuration;
P is the transmural pressure (with low perivascular pressure); and
f is the axial force that maintains the axial "prestretch" of the vessel.

With respect to Equation 2, the importance of the thickness:lumen ratio (h/a) becomes self-evident, noting that h is total thickness, not merely intimal-medial thickness. With respect to Equation 3, the importance of wall cross-sectional area becomes evident, which is often reported with regard to "eutrophic" versus "hypertrophic" vascular remodeling. Finally, while the importance of axial stretch in hypertension was recognized at least 15 years ago, it has received surprisingly little attention, most likely due to the inability to reasonably infer specific values in vivo. Large arteries appear to maintain these stresses near homeostatic values (e.g., on the order of 1.5 Pa for $\tau_w$ and 100 kPa for both $\sigma_\theta$ and $\sigma\sigma_z$ in specific arteries, where 1 kPa=7.5 mm Hg).

The Humphrey Paper proposes relating perturbed values of flow Q and pressure P to original values via $Q=\varepsilon Q_0$ and $P=P_0$, where a subscript$_0$ or superscript$^0$ denotes original and $\varepsilon$ and $\gamma$ denote sustained percent changes from original (e.g., $\gamma=1.3$ if P increases 30% from original).

While Equations (1)-(3) above suggest that if mean shear stress, as well as mean circumferential stress, are restored via growth and remodeling processes, then specific morphological changes to large arteries can perhaps be mathematically modeled as follows:

Analysis Step No. 1:

If: $\tau_w = 4\mu\varepsilon Q_0/(\pi a^3)$ (perturbed state)  (Equation 4)

And: $\tau_w^0 = 4\mu Q_0/(\pi a_0^3)$ (original state)  (Equation 5)

Then: $\tau_w = \tau_w^0$  (Equation 6)

Requires: $4\mu(\varepsilon Q_0)/(\pi a^3) = 4\mu Q_0/(\pi a_0^3)$  (Equation 7)

Therefore: $a = \varepsilon^{1/3} a_0$  (Equation 8)

Analysis Step No. 2:

If: $\sigma_\theta = (\gamma P_0)\left(\varepsilon^{\frac{1}{3}} a_0\right)/h$ (perturbed state)  (Equation 9)

And: $\sigma_\theta^0 = (P_0 a_0)/h_0$ (original state)  (Equation 10)

Then: $\sigma_\theta = \sigma_\theta^0$  (Equation 11)

Requires: $(\gamma P_0)\left(\varepsilon^{\frac{1}{3}} a_0\right)/h = (P_0 a_0)/h_0$  (Equation 12)

Therefore: $h = \varepsilon^{1/3}\gamma h_0$  (Equation 13)

Applying certain of the Equations 1-13 cited above, a 30% sustained increase in flow alone should produce a 9% increase in both caliber and wall thickness. In contrast, a 30% sustained increase in pressure alone should produce a 30% increase in thickness but no change in caliber. In other words, a mean stress-mediated growth and remodeling response would require coordinated changes in luminal radius a and wall thickness h based directly on the percentage of perturbations in hemodynamics from the original state.

There is a complex biological interplay associated with sustained hemodynamic vascular changes in either flow or pressure, which effectively serve as the means by which lumen radius tends toward $\varepsilon^{1/3} a_0$ and thickness tends toward $\varepsilon^{1/3}\gamma h_0$.

If luminal radius and wall thickness are dictated by flow and pressure, then restoring axial wall stress $\sigma\sigma_z$, to its original value requires a change in axial force f, which typically would cause a change in length (e.g., possible vessel tortuosity).

The general assumption that all of the various responses to each of the above-mentioned stresses must be considered together is reinforced by real world observations, coupled with certain identifiable changes produced at the cellular and tissue levels due to the influence of change in vascular pressure (e.g., cyclic circumferential stress or strain) and vascular flow (i.e., WSS).

While most of the previous vascular research concerning arterial biology and mechanics has been focused on endothelial and smooth muscle cells, there is increasing evidence that adventitial fibroblasts play a significant role in vascular homeostasis, as well as in disease progression.

Vascular mechano-biology requires consideration of these sustained hemodynamic vascular changes in either flow or pressure, and the complex short-term and long-term cellular responses which they provoke, including for example, altered proliferation, migration, differentiation, apoptosis, synthesis and degradation of matrix, cross-linking of matrix, integrin binding that governs cell-matrix interactions, and cadherin activity that governs cell-cell interactions.

Medical literature has reported an ever-increasing sigmoidal relationship between increased WSS ($\tau_w$) and endothelial NO synthase mRNA, and a decreasing sigmoidal relationship between increased WSS ($\tau_w$) and endothelin-1 (ET-1) mRNA.

A complex interplay with respect to changes in vasodilator/vasoconstrictor responses appear to be regulated by various vascular parameters, including:

a) Increases in WSS ($\tau_w$) provoke increases in endothelial production of NO, which in turn acts as an inhibitor of smooth muscle cell proliferation.

b) Increases in cyclic stretch provoke increases in endothelial production of ET-1.

c) Increases in cyclic strain provoke increases in endothelial production of endothelial NO synthase.

d) Increases in WSS ($\tau_w$) provoke decreases in endothelial ET-1 production, which decreases the influence that ET-1 would otherwise have to promote smooth muscle cell proliferation and synthesis of collagen.

e) Because WSS and cyclic circumferential stretch can change simultaneously in vivo, analysis of vasoaltered states is presently approached by reliance on more simplified biomechanical models.

By way of example, the influence of local increases in blood flow above normal limits will now be discussed. As noted earlier, the endothelium up-regulates endothelial NO synthase, and increases its production of NO in response to local increases in blood flow above normal limits, which in turn causes the vascular wall to dilate in an effort to restore WSS ($\tau_w$) toward the original levels. Once flow returns to normal levels, NO production returns to normal, and the vessel regains its original caliber according to a normal vasoactive response.

In the event, however, that the local increase in flow is sustained, such as during vigorous exercise, the increased production of NO enables cell and matrix reorganization or turnover to occur in the dilated state. Hence, combined WSS ($\tau_w$) and intramural stress-mediated growth and remodeling in a sustained vasodilated state allows the vascular wall to become entrenched at a larger radius and wall thickness. Assuming blood-flow induced WSS ($\tau_w$) eventually normalizes, NO production levels return to normal, and the biomechanics are reset to tensional homeostasis.

By way of alternate example, the influence of local increases in blood pressure above normal limits will now be discussed. While large arteries are nearly elastic, and thus distensible, an initial local increase in blood pressure tends to increase the luminal radius and isochorically decrease thickness. These changes serve to increase blood-pressure induced circumferential wall stress $\sigma_\theta$, which sets into motion a cascade of cellular-based stress-mediated responses, produces accelerated growth of smooth muscle cells, and potentially endothelial and fibroblast cells, resulting in significant vascular remodeling.

Yet, the initial pressure-induced increase in caliber would likely decrease blood-flow induced WSS ($T_w$), which would then tend to decrease endothelial production of NO, while increasing production of ET-1 to restore WSS ($T_w$) toward normal levels. Wall thickening thus occurs in an initially constricted state at the original caliber via increases in smooth muscle (i.e., hyperplasia and/or hypertrophy) driven by stress-mediated increases in platelet-derived growth factor (TGF-$\beta$) and extracellular matrix (e.g., particularly fibrillar collagens driven by increases in TGF-$\beta$, connective tissue growth factors, etc.). Hence, the vascular wall again becomes entrenched within a vasoaltered state, with multiple stresses simultaneously playing important roles. Once the wall has thickened sufficiently to restore circumferential wall stress $\sigma_\theta$, toward original conditions (i.e., the increased ability of the wall to withstand the increased pressure), at a stable caliber and WSS ($T_w$), the endothelium can return to its normal production of NO.

More specifically, the influence of WSS with respect to in-stent restenosis (ISR) was studied and reported as a significant negative correlation between NT and WSS in a majority of the patients studied. Sanmartin M., et al. Influence of Sheer Stress on In-Stent Restenosis. Revista Espanola De Cardiologia. 2006; 59(1): 20-7, the disclosure of which is hereby incorporated by reference. In particular, the proliferation of scar tissue produced within the arteries following angioplasty, even without subsequent stenting, was triggered due to damage resulting from the mechanical stretching of the vessel wall (i.e., angioplasty), which exposed subendothelial structures to blood flow and activation of a major thrombotic and inflammatory response. The additional process of stenting the revascularized vascular site, produced significant vessel damage and trauma to the vessel.

Moreover, the amount of neointimal proliferation was proportional to the degree of damage caused, and local factors played a major role in the reparative response following angioplasty. The presence of the stent implant at the luminal surface contributed to the increased neointimal response, (even the design of the stent can influence this response). While other factors, such as systemic variables (e.g., diabetes, genetic polymorphisms, diet, exercise and the like) also contributed to the risk of restenosis, the role of fluid dynamics relative to neointimal proliferation was of real consequence to the progression of restenosis. Neointimal proliferation was highly correlated to relatively low WSS values at the vascular treatment site. The reduced WSS levels at either the proximal and distal edges of the stent implant also corroborated that these local hemodynamics accounted for lumen loss due to the progression of NT, which leads to in-stent restenosis (ISR).

In 2012, a relatively sophisticated series of vascular studies were reported regarding patients receiving bioresorbable vascular stent (BVS), formed of a polymer scaffolding comprising poly-lactide. Brugaletta S. et al. Vascular Compliance Changes of the Coronary Vessel Wall After Bioresorbable Vascular Scaffold Implantation in the Treated and Adjacent Segments. Circulation Journal. 2012; 76: 1616-23, the disclosure of which is hereby incorporated by reference herein.

The compliance of each vessel was calculated for each vessel segment (i.e., segment proximal and abutting the proximal edge of the implanted stent, segment directly supported by the stent scaffold, and the segment distal and abutting the distal edge of the implanted stent). With respect to the measured change in vessel compliance that was observed at the moment immediately prior to implantation of the BVS stent, when compared to the vessel compliance immediately after stent implantation, it was not surprising to observe the most significant difference was observed at the stented/scaffolded vessel segment. It was also not surprising that compliance mismatch immediately following stent implantation was most pronounced at the junction located between the proximal edge of the stented/scaffolded segment extending into the proximal segment, as well as the junction located between the distal edge of the stented/scaffolded segment extending into the distal segment.

With respect to the patients treated by the BVS 1.0 stent, for example, a significant increase in vessel compliance was observed at the segment that was initially stented. The relatively pronounced increase in vessel compliance observed at the late follow-up intervals was primarily attributed to the gradual disappearance of the bioresorbable stent scaffolding.

It is believed that with the bioresorption of the BVS stent, the vessel segment revascularized is eventually able to recover some of its native vessel compliance and thereby better influence improved WSS levels to mitigate against restenosis. Additionally, with the eventual bioresorption of the polymer scaffolding, it is believed that the initial compliance mismatch observed between the vessel segment stented, in comparison with the adjacent proximal and distal segments, may eventually equalize, as well as a gradual dissipation of flow disturbances and heterogeneous distribution of WSS once the stent implant has fully resorbed.

In addition to needed improvements in revascularization of CAD, revascularization of the superficial femoral artery (SFA) also remains among the most challenging anatomy. The superficial femoral artery (SFA), for example, is certainly one of the most challenging peripheral vascular situations to revascularize. This is due to the fact that SFA lesions are typically quite diffuse, extending between 8-25 cm, and usually presenting calcified plaque. SFA patients often present with symptoms of claudication, which is defined as reproducible ischemic muscle pain, which often occurs during physical activity and is relieved after rest. The claudicant experiences pain because of inadequate blood flow.

Pulsatility is the fluctuation of blood pressure and blood flow velocity during systole and diastole. As blood is pumped through the coronary vessels, the vessel wall is exposed to two sets of forces, both of which are critically important, namely: (a) WSS, which is the frictional force generated on the intimal surface of the vessel wall as the blood flows through it; (b) cyclic strain, which is the force generated by the stretching of the vessel wall during systole and is affected by vessel distensibility (i.e., stretchability); and (c) the interplay of WSS and cyclic strain controls fundamental cell signaling which either leads in the positive direction of atheroprotective/thromboresistant changes, or in the negative direction of disease progression and instability.

For instance, cyclic strain is known to stimulate eNOS gene regulation, and steady-state levels of prostacyclin are significantly increased if the WSS force is applied in a pulsatile fashion, in contrast to a relatively steady laminar flow rate.

Consequently, it is believed that cell signaling may become undesirably altered at locations where interactions between stent scaffolding and overlying vascular tissue result in excessive inhibition of vascular distensibility. These complex bio-feedback mechanisms which translate mechanical/fluid dynamics forces into pertinent chemical cell signals is referred to as "mechanotransduction."

Additionally, it is understood that applied mechanical strain preferentially preserves collagen fibrils, and stretch of the vascular wall stimulates increased actin polymerization, activating the synthesis of smooth muscle-specific protein. Under such conditions, smooth muscle cells preferentially maintain their contractile phenotype, while such differentiation is lost in sites of vascular injury (i.e., atherosclerosis or restenosis).

In summary, therefore, it is believed that the present invention provides a system and method to revascularize diseased arteries in a manner which acutely improves outcomes significantly. Among the most important aspects of the present invention, the following unique advantages are noted relative to vascular compliance:

The present invention utilizes a composition which is infused by catheter into the vascular treatment site prior to vessel dilatation, and which penetrates both plaque and vascular tissues. It has been observed that the composition readily penetrates calcified plaque, and produces a modified, pliable plaque which more readily responds to the subsequent PTA dilatation.

The present invention provides a novel technology by which the dilated vascular treatment site is stabilized for purposes of luminal gain retention, but without the need of implanting a stent-like prosthetic. The present invention achieves an immediate or acute restoration of vascular compliance (i.e., pulsatility/distensibility) approaching normal, healthy vascular behavior. Consequently, it is expected that this will facilitate a positive healing response, not only because this procedure enables retention of luminal gain without the need of a traumatic implantation of a prosthetic vascular stent scaffolding, but because the endothelium may experience an immediately favorable cellular environment in which positive chemical signals will follow (e.g., NO, prostacyclin, tissue plasminogen activators, thrombomodulin), thereby promoting healthy WSS levels, inhibiting smooth muscle cell proliferation, and minimizing inflammation.

The present invention improves the vascular healing response of diseased vasculature in general, following revascularization procedures. This new therapy provides an acute interventional function (i.e., during the interventional revascularization procedure) to reinforce vascular tissue (e.g., natural vascular scaffolding comprising collagen and elastin fibrils disposed throughout the vascular wall structure of both arteries and veins), as an adjunct to interventional procedures. The disclosed processes may have the ability to retain luminal gain following angioplasty, without the necessity of implanting either a permanent metallic stent, or a bioresorbable stent. Consequently, activation of the disclosed compound may not only provide an alternative approach to retention of luminal gain following angioplasty, without the necessity of implantation of a permanent or resorbable stent, but may serve to also stabilize and fixate the remodeled plaque to prevent embolic events.

This new therapy provides an acute interventional function (i.e., during the interventional revascularization procedure) to acutely restore vessel compliance at the treatment site. In stark contrast to the chronic difficulties associated with permanent prosthetic stent-like implants, such as BMS and DES, the present invention can restore the vessel compliance at the revascularization treatment site.

Due to the unique nature of the present interventional therapy, it may not be necessary to deploy any stent implant, either permanent or bioresorbable. By avoiding the necessity of implantation of a stent, a substantial portion of the vascular trauma associated with stent deployment, as well as the potential for ISR, can be entirely avoided. Contrary to implantable resorbable stents, which requires several months to fully bioresorb, using the present invention the treated vessel can immediately commence its healing response.

Moreover, since the revascularization procedure using the present invention virtually eliminates any need for an atherectomy procedure to prepare the vessel for angioplasty and stenting, as well as eliminating the need for stent implantation, a more prompt and improved healing response can be expected due to the elimination of the majority of vascular trauma using conventional revascularization techniques.

For many of the reasons stated above, it may become completely unnecessary to administer various pharmaceutically active agents, such as anti-proliferatives, to manage the inflammatory response resulting from stent implantation.

Finally, with the prospect of eliminating prosthetic stent implants, and accomplishing revascularization with substantially reduced vascular trauma, the possibility has finally arisen that patients might be able to safely discontinue the anti-platelet regimen within the a period of only 90 days following revascularization.

The present invention is directed to a naphthalimide compound comprising a solubilizing functional group. Without being bound to any particular theory, it is hypothesized that the naphthalimide compound may disrupt the crystal structure of the inorganic portion of the atheromatous plaque by drawing calcium from the crystal structure thereby weakening and softening the plaque. This softening may facilitate additional compression of the plaque during treatment of the blood vessel thereby resulting in less damage to the blood vessel, which is known to be the result of hard and sharp pieces of the calcified plaque disrupted by balloon angioplasty.

The naphthalimide compound may comprise a hydrophobic component that allows the compound to penetrate the greasy portion of the plaque and access the calcium crystalline matrix. The disclosed naphthalimide compound may have a higher affinity for calcium. The structure of the disclosed compound may allow it specifically bind to calcium and other alkali earth metals, allowing it to cross the membrane of cells, i.e., can be used to control calcium concentration inside the cell.

The naphthalimide compound may be a 4-amino-1,8-naphthalimide compound having a structure selected from the group consisting of:

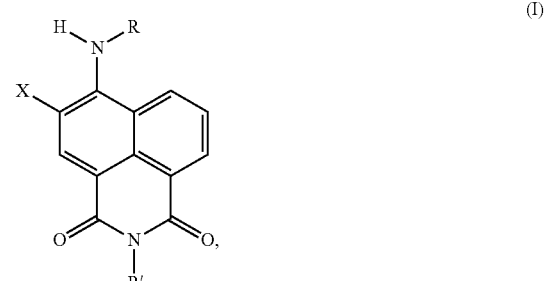

(I)

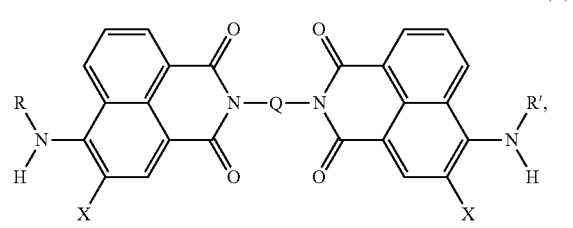

(II)

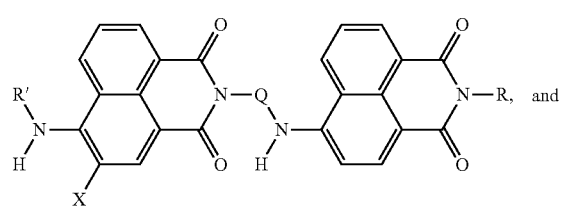

(III)

-continued (IV)

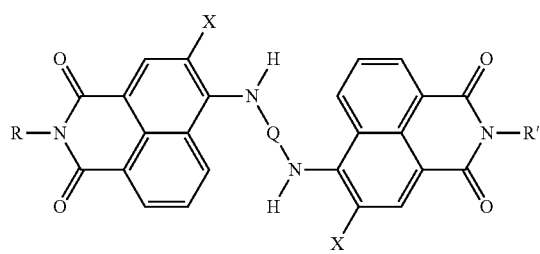

wherein R, R', and Q are each independently selected from the group consisting of straight-chain and branched chain alkyl groups having from 2 to 200 carbons, optionally substituted with one or more ether, amide or amine groups; and wherein X is hydrogen. Naphthalimide compounds which may be used include those described in U.S. Pat. Nos. 5,235,045; 5,565,551; 5,776,600; 5,917,045; 6,410,505; 7,514,399; and 8,242,114, the disclosures of all of which are hereby incorporated by reference.

In an aspect, R' can be a substituted alkyl group, wherein the alkyl group is substituted with heteroatoms, such as N, O, P, and S or halogens, such as F, Br, Cl, or I. In another aspect, R' can include an amine, a carboxylate, a phosphate, and/or a sulfate.

In an aspect, Q is a polyethylene moiety. Moreover, Q can be a moiety that contains amines and carboxyl groups arranged in a fashion reminiscent of EDTA-like ligands, phosphate groups and/or organic acids arranged in a fashion able to interact with calcium, or functional motifs able to interact with calcium such as luciferin.

In another aspect, Q is an acid or an alcohol, but can also be a thioester, an organophosphorous ester, an anhydride, an amide, a carbamate, or an urea. In another aspect, the naphthalimide compound has the following structure:

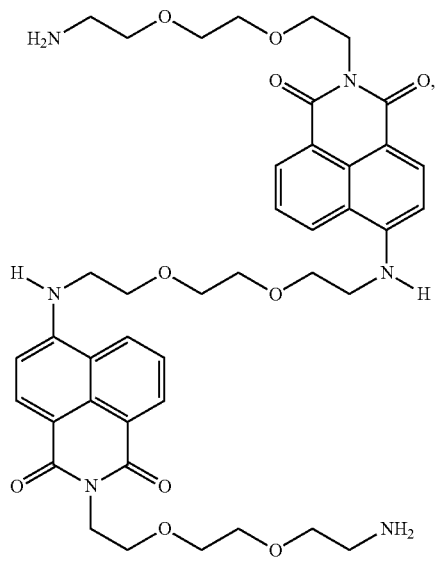 [SMILES: NCCOCCOCCN1C(=O)c2cccc3c(NCCOCCOCCNc4ccc5c6c(cccc46)C(=O)N(CCOCCOCCN)C5=O)ccc(c23)C1=O]

or its geometrical isomers. In some embodiments, the naphthalimide compound has the following structure:

(V)

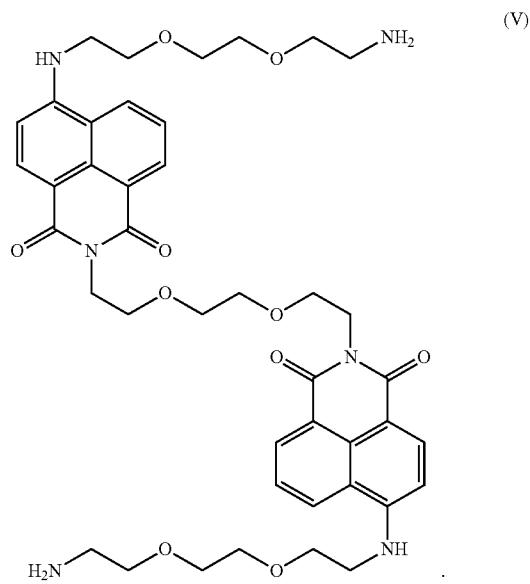 [SMILES: NCCOCCOCCNc1ccc2c3c(cccc13)C(=O)N(CCOCCOCCN1C(=O)c3cccc4c(NCCOCCOCCN)ccc(c34)C1=O)C2=O]

It is hypothesized that upon photoactivation the polyethylene moiety linking the two naphthalimides becomes an intermediate with photoactivated terminal amines. This intermediate has an affinity for binding to amino acid residues on biological molecules, and forms the linkage via a condensation reaction. In particular, the naphthalimide may have a higher affinity for linear protein structures such as collagen or elongated elastin when compared to globular proteins, such as albumin, because the constant twisting and turning of the backbone pulls the hydrogen bonds "out of phase". Moreover, the dimer, shown above, penetrates plaque easily and the diffusion rate is minimally constrained The polyether moieties attached in the imide positions impart solubility and the naphthalimide rings are for photoactivation. The solubilizing tails are also believed to mimic a crown ether effect present in known chelating agents. Thus, it is believed that these solubilizing tails would have the ability to penetrate the crystalline regions and disrupt the structure that makes the plaque hard and sharp. To be clear, however, there is a balancing act to be achieved between solubility and diffusion that must be considered in formulating compounds for use in the present invention.

Below are some additional compounds including a monomer, dimer, and trimer of naphthalimide rings. Polymers and derivatives of the compounds below are also contemplated.

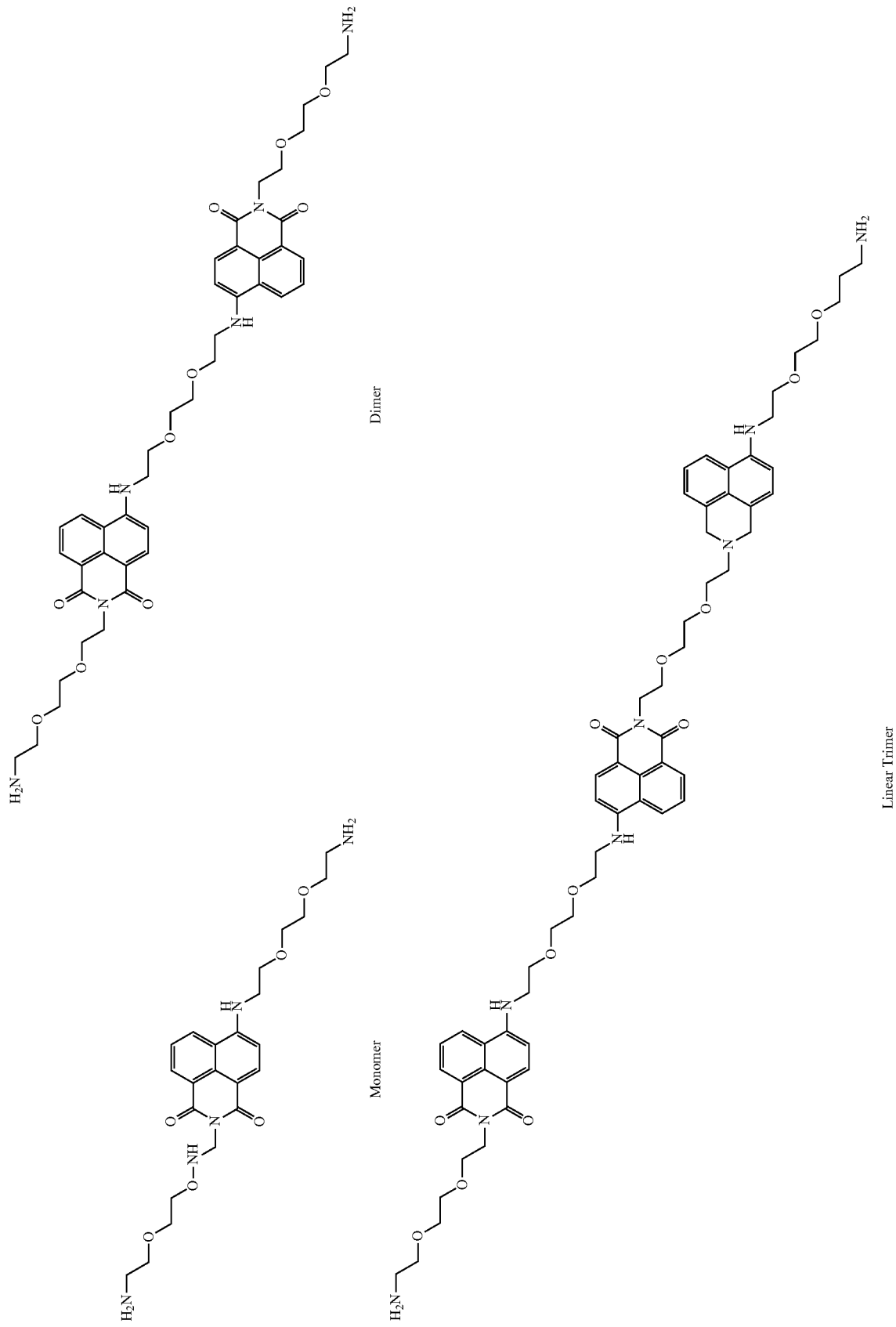

The dimeric structure of the disclosed naphthalimide compound is designed to lie along the extended backbone of the collagen helix as shown below.

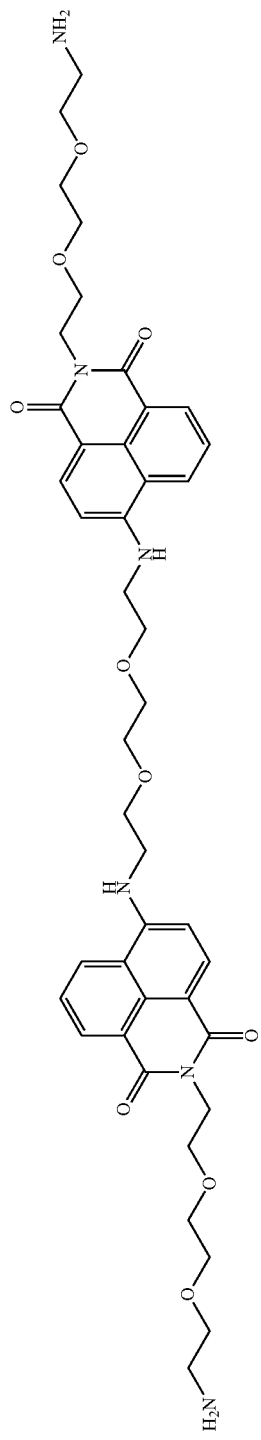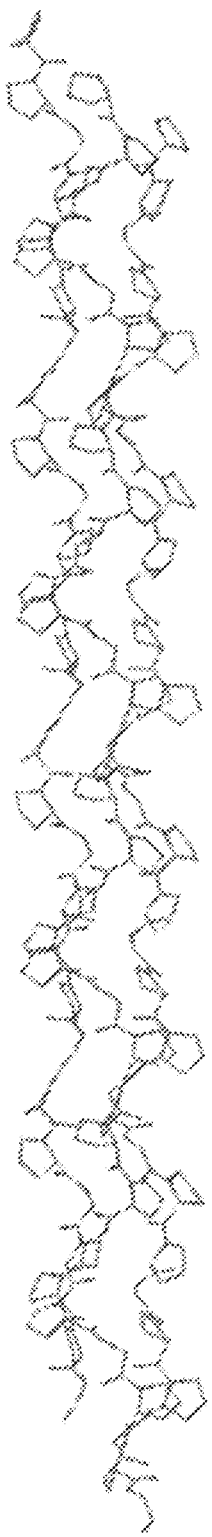

In considering alternative compounds for use in the disclosed composition, it is noted that as molecules get longer, at some point the strong hydration associated with the terminal amines and the weaker hydration associated with the oxygen atoms will fail to overcome the insolubility of the greasy naphthalimide and the naphthalimide will be insoluble and therefore not useful. In particular, as the molecule becomes longer and therefore more "greasy" it will more likely stick to one collagen molecule and not span the gap between two collagen molecules. For this reason, linear trimers, such as exemplified above, may not be preferred.

In order to overcome the challenges of longer compounds, like a linear trimer, a "capped" trimer, as shown below, comprising no terminal amines and the polyethylene groups have been changed to polypropylene groups may be used. This molecule may have a smaller hydrodynamic radius and it may be more hydrophobic. This may present an advantage in faster diffusion and an ability to penetrate plaque more effectively. The downside may be reduced water solubility.

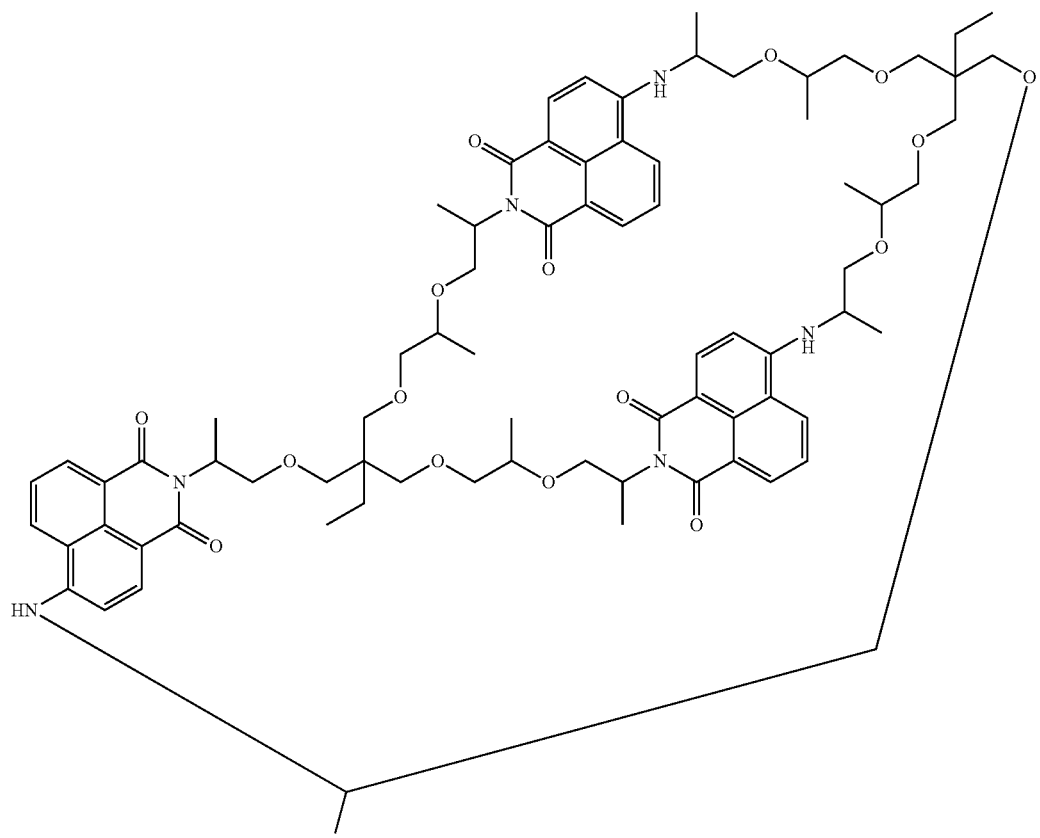 [SMILES: CCC12COCC(C)Nc3ccc4c5c(cccc35)C(=O)N(C4=O)C(C)COCC(CC)(COCC(C)OCC(C)N3C(=O)c4cccc5c(ccc(c45)C3=O)NC(C)COC(C)COC1)COCC(C)OCC(C)N1C(=O)c3cccc4c(ccc(c34)C1=O)NC(C)COC(C)COC2]

A "starred timer" having two terminal amines, but not in a linear arrangement can be used as a compound of the invention. In addition, it is believed that this design increases the likelihood of linking with collagen molecules. This behavior is not obvious from the monomer and dimer structures. Derivatives and polydisperse isomers of the compound below are also contemplated.

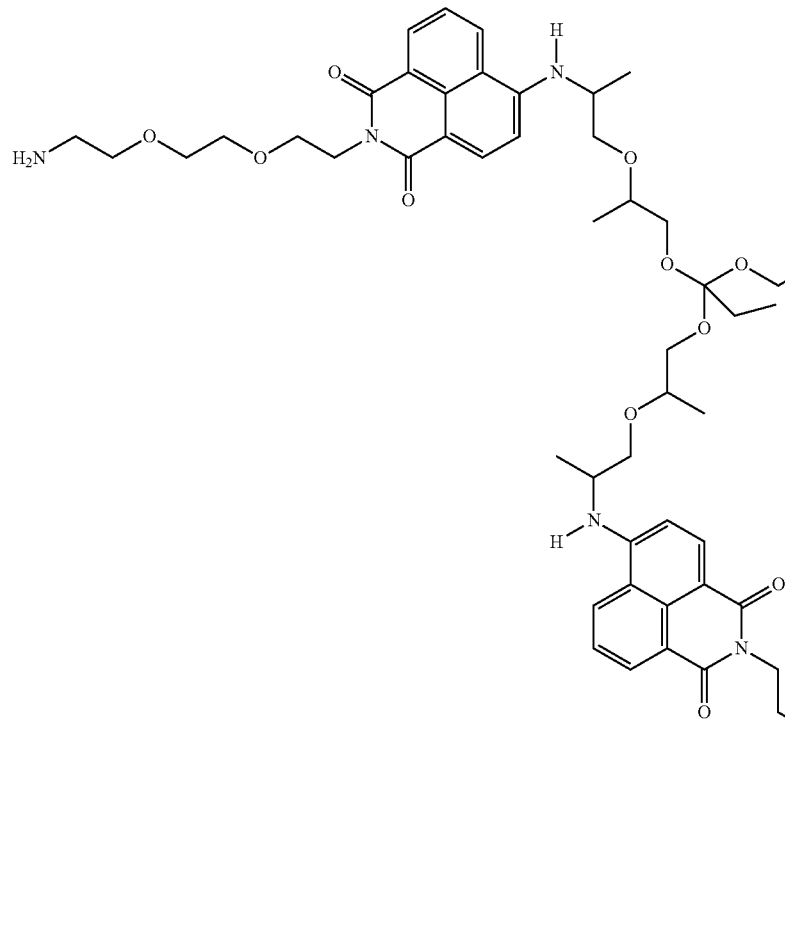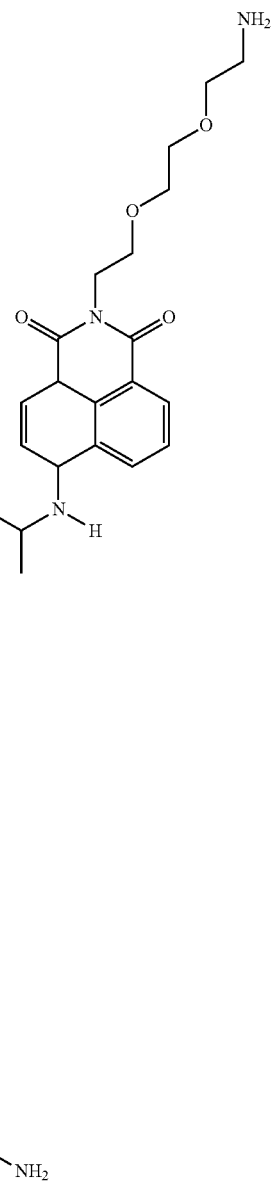

The "starred" trimer is designed to overcome any intramolecular links that may form between the compound and the collagen matrix. The center group of that will become the linker retains the polyether functionality but the branched nature and additional methyl groups may reduce the tendency of the linker to hydrogen bond to the collagen backbone while retaining the ability to associate with water. These characteristics may increase the likelihood of collagen intermolecular bonds and thereby increase the effectiveness of the compound.

The "starred timer" extending along a collagen matrix is shown below. With this compound, the water solubility might be lower, the diffusion rate might be slower or the preferential localization with collagen might be lower. Derivatives of the compound below are also contemplated.

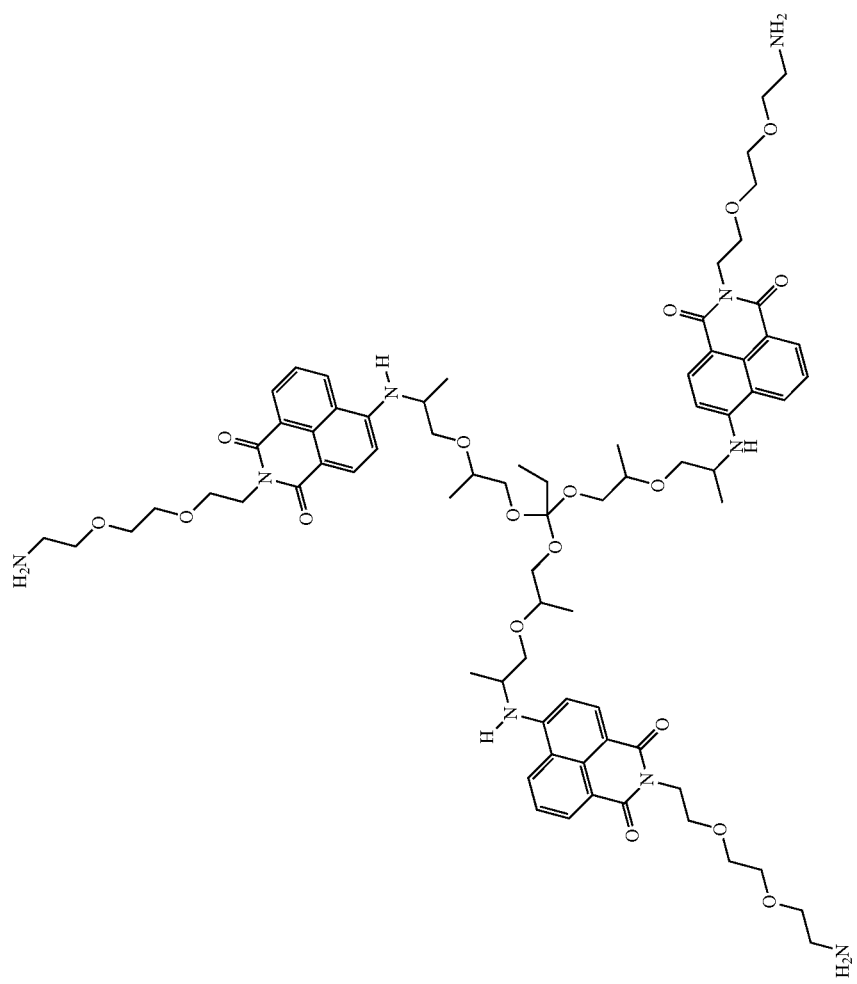

Compounds other than the naphthalimide compounds disclosed above and their derivatives are also contemplated for use in a composition. In particular, compounds that possess functional groups that allow for water solubility, increased tissue diffusion, and calcium solubilization are considered useful for the present invention. Exemplary compounds, include but are not limited to, EDTA-like ligands, luciferin based ligands, polyether ligands, phosphate based ligands, and organic acids.

Ethylenediaminetetraacetic acid (EDTA) is a member of the polyamino carboxylic acid family of ligands. EDTA binds to metals in a hexadentate fashion with an octahedral Coelenterazine-WS, a luciferin based ligand, is an additional compound that can be used and is also supplied by Donjindo Molecular Technologies.

A suitable polyether ligand for use as a compound in the present invention may be Calcium ionophore V—Selectophore® (10,19-Bis[(octadecylcarbamoyl)methoxyacetyl]-1, 4,7,13,16-pentaoxa-10,19-diazacycloheneicosane), as shown below. This particular compound has long chain alkyl groups attached that provide lipid solubility allowing the compound to transport calcium across cell membranes.

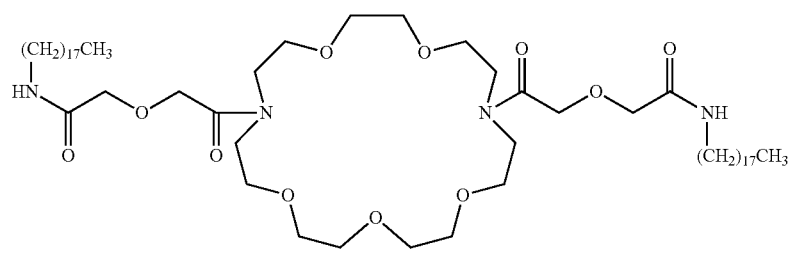

geometry. Numerous variants of this basic structure have been used by chelating agents with various affinities for different metals, such as calcium. Examples of compounds having a basic structure similar to EDTA, include but are not limited to, ethylene glycol tetraacetic acid (EGTA); diethylene triamine pentaacetic acid (DTPA); 1,2-bis[o-aminophenoxy)ethane-N,N,N'N'-tetraacetic acid (BAPTA); and Amino-5-(3-dimethylamino-6-dimethylammonio-9-xanthenyl)phenoxy]-2-(2-amino-5-methylphenoxy)ethane-N,N,N', N'-tetraacetic acid. EDTA is completely hydrophilic and it is expected that it cannot penetrate the greasy portion of plaque. Moreover, a relatively low binding constant (10.69 log $K_f$) between EDTA and calcium renders it unlikely that EDTA would be capable of removing calcium from plaque in a blood vessel.

Additional compounds, known for their use in fluorescence imaging, can be used and comprise four carboxylic acid functional groups, such as Fura 2 ($C_{29}H_{22}N_3O_{14}^{5-}$), which binds to free intracellular calcium; Fura 2-AM ($C_{44}H_{47}N_3O_{24}$); Fluo 3 ($C_{36}H_{30}Cl_2N_2O_{13}$); Fluo3-AM ($C_{51}H_{50}Cl_2N_2O_{23}$); Indo 1 ($C_{32}H_{31}N_3O_{12}$); Indo 1-AM ($C_{47}H_{51}N_3O_{22}$); Quin 2 ($C_{26}H_{23}K_4N_3O_{10}$); and Rhod 2-AM ($C_{52}H_{59}ClN_4O_{19}$). These compounds are available from suppliers such as Donjindo Molecular Technologies. The conjugated aromatic group provides a fluorescence. The added aromatic group teaches that changes can be made to the structure of the compound without compromising the ability to soften plaque. Moreover, these groups are inherently greasy and therefore lipid soluble, which may provide the ability to penetrate tissue.

Variants of the crown ether motif have been reported by Gatto et al, II, J.A.C.S., vol. 106, No. 26, pp. 8240-8244 (1984) and Capel-Cuevas, et al, Talanta, Vol 78, pp. 1484-1488 (2009). These reports demonstrate that both the substituents as well as the constituent chalcogen can be varied and still provide the ability to chelate calcium.

Phosphate based ligands, such as phosphonates or phosphonic acids, have been used to chelate calcium to prevent scale in water systems. Some exemplary compounds that may be useful as compounds in the present invention, include but are not limited to, etidronic acid (INN) or 1-hydroxyethane 1,1-diphosphonic acid (HEDP); aminotris (methylenephosphonic acid) (ATMP); ethylenediamine tetra (methylene phosphonic acid) (EDTMP) (a phosphonate analog of EDTA); and diethylenetriamine penta(methylene phosphonic acid) (DTPMP).

Organic acids suitable for use as a compound of the present invention include, but are not limited to, citric acid and dipicolinic acid (pyridine-2,6-dicarboxylic acid or PDC).

Common chelating agents include desfuroxamine mesylate (used for iron toxicity, dimercaprol (BAL) (lead, preferred for arsenic and mercury), DMSA—an analogue of dimercaprol (given for lead and arsenic), D-penicillamine (for lead, arsenic, or mercury), and calcium disodium versante (CaNa2-EDTA). However, these compounds are generally used to chelate metals other than calcium, and may not have the requisite chemical structure to be water soluble and penetrate tissue, as needed by compounds of the present invention.

The disclosed naphthalimide compounds and alternative plaque-softening compounds can further comprise a tether linkage to a pharmacological agent. In particular, a pharmacological agent can be attached to the 4-amino group of a naphthalimide compound through a tether. Upon activation by an activating agent, the amino group containing the tether and pharmacological agent can be controllably released in an active form that will bond to tissues localizing the delivered pharmacological agent on the target tissue. To be clear, the pharmacological agent can be released over time depending on hydrolytic cleavage, photolysis cleavage, enzymatic cleavage, or a combination of hydrolytic cleavage, photolysis cleavage, and enzymatic cleavage of the pharmacological agent. The localization, solubility, and release profile of the pharmacological agent can be tailored by synthesis of the appropriate tether. The reaction scheme is exemplified in FIG. 1. The localization, solubility, and release profile of the pharmacological agent can be tailored by synthesis of the appropriate tether.

Figure 2A:
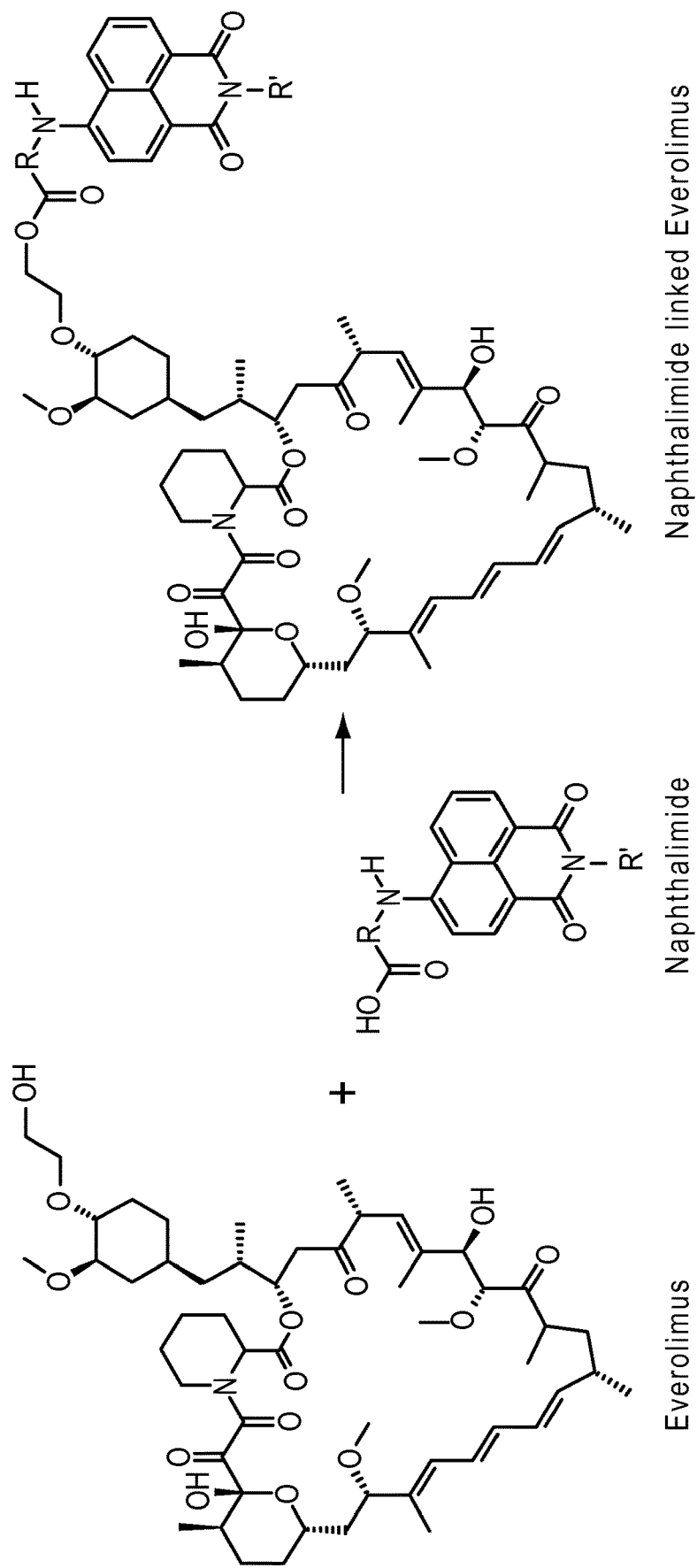
FIGS. 2a and 2b illustrate exemplary synthetic pathways for plaque-softening compounds tethered to pharmacological agents.
Figure 2B:
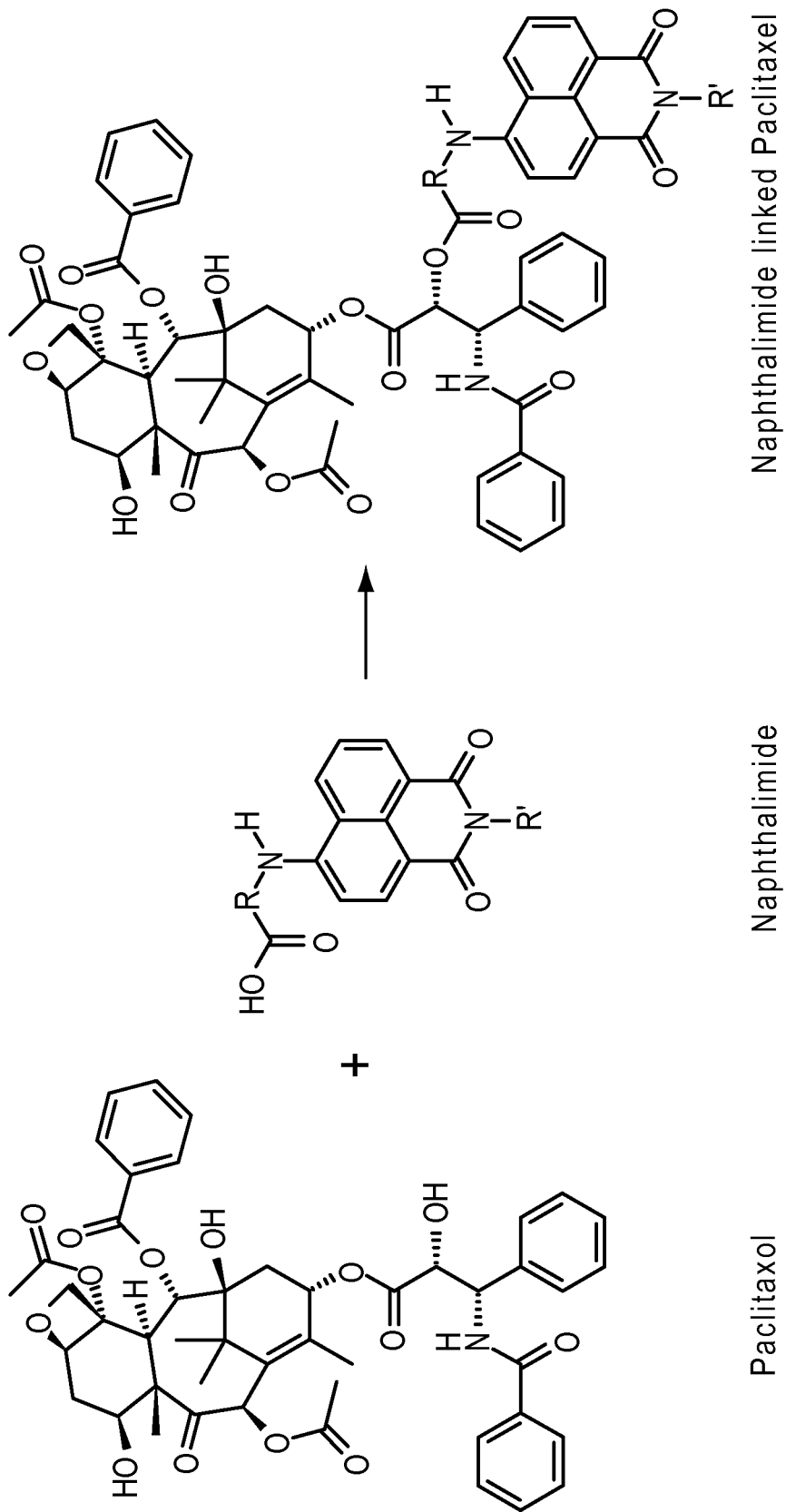

FIG. 2A illustrates a synthetic pathway for the production of the naphthalimide tethered to everolimus. FIG. 2B illustrates a synthetic pathway for the production of the naphthalimide tethered to paclitaxel. The reaction would be conducted with a DCC catalyst in organic solvent with purification to be complete on a silica gel column. The functional group R (the tether) and the R' (the tail optimized for localization and solubility) will be chosen to impart the needed characteristics to the molecule. The tether R will control the rate of hydrolysis and the solubility and R' will control the water solubility of the compound.

An important consideration in the choice of R is the relationship between the structure and the hydrolysis rate. Table 1 describes six possible tethers with anticipated hydrolysis rates that vary from slow to fast. The initial synthesis will center around conjugates with the tether derived from compounds 3 and 5. When used, R' can be a polyether, JEFFAMINE® M-600 available from Huntsman. However, it is understood that other R' groups may be used to solubilize the resultant compound.

TABLE 1

Structure and anticipated hydrolysis rates of linkers.

| # | Linker Structure | Source of Linker | Anticipated Cleavage Rate | Increasing Rate Of Hydrolysis/ Faster Drug Delivery |
|---|---|---|---|---|
| 1 | HO-C(=O)-CH$_2$-NH$_2$ | Linker available from Sigma-Aldrich Glycine | Slow | ↓ |
| 2 | HO-C(=O)-CH$_2$-CH$_2$-NH$_2$ | Linker available from Sigma-Aldrich 3-Amino-propionic acid | Slow | |
| 3 | HO-C(=O)-CH$_2$-S-CH$_2$-NH$_2$ | In situ generated | Expected $t_{1/2}$ ~15 days Good for 30 day release | |
| 4 | HO-C(=O)-CH(OH)-CH$_2$-NH$_2$ | Linker available from Sigma-Aldrich 3-amino-2-hydroxy-propionic acid | | |
| 5 | HO-C(=O)-S-CH$_2$-NH$_2$ | In situ generated | Expected $t_{1/2}$ ~4 days Good for 7 day release | |
| 6 | HO-C(=O)-O-CH$_2$-NH$_2$ | In situ generated | Fast | |

Compounds 1 and 2 are expected to form simple ester tethers. These esters are expected to hydrolyze only slowly at physiological pH. In the unlikely situation that the local environment increases the hydrolysis rate to a level where the drug is delivered too quickly, these tethers could be used to slow that rate.

Compound 3 has an electron withdrawing substituent near the carboxylic acid which will become part of the ester targeted for hydrolytic cleavage. The electron withdrawing group will speed the reaction from compounds 1 and 2. This tether will be synthesized as part of the naphthalimide structure in situ before attachment to a pharmacological agent, such as everolimus. Literature reports show a hydrolysis rate that is well suited to a 30 day delivery. The full structure of this conjugate is shown below including the R' tail.

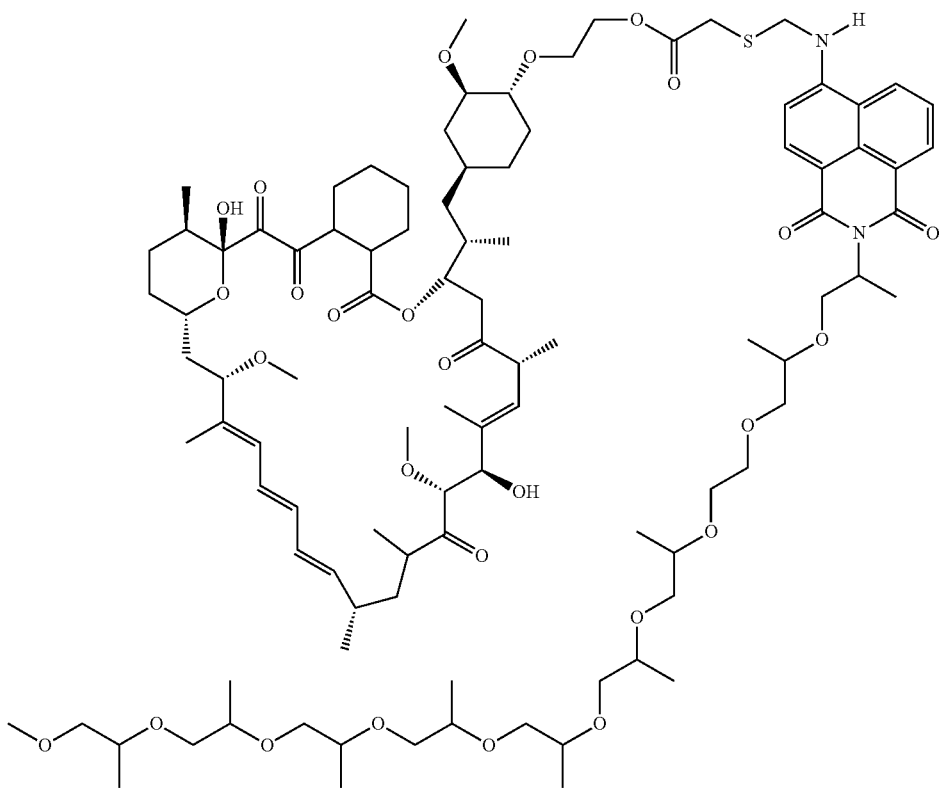

Compound 4 has additional electron withdrawing characteristics when compared to compound 3. This will provide a rate of hydrolysis that is somewhat faster than compound 3 and represents an example to tailor the release rates.

Compound 5 has a structure that is even more susceptible to hydrolysis and can provide a faster rate of release. This tether can be synthesized as part of the naphthalimide structure in situ before attachment to a pharmacological agent. Literature reports show a hydrolysis rate that is well suited to a 7 day delivery.

Of the compounds shown in Table 1, compound 6 will have the fastest release rate, likely too fast for a seven day delivery but represents a possible structure if the local environment stabilizes the ester and release rates are unexpectedly slow.

In an aspect, the nitrogen of the 4-amino naphthalimide connected to the tether can attach to the tissue after activation by an activating agent. The activating agent is selected from radiated energy, electromagnetic energy, laser, electric current, electrons, thermal neutrons, and chemicals. The tether/pharmacological agent will remain covalently attached to the tissue, likely collagen until such time that the collagen is turned over. Hydrolysis of the ester linkage will result in the release of the pharmacological agent in an unaltered state.

Localization of the compound with the tethered drug is controlled primarily by the characteristics of the imide substituent. As an example, polyether functional groups, which are hydrophilic, may increase the solubility of the pharmacological agent and may direct the localization to collagen rich regions, such as an arterial wall. Such a hydrophilic compound may easily enter the luminal side of an arterial wall and may penetrate into the media. Alternatively, a hydrophobic compound may encounter a luminal barrier and be excluded from the media.

The pharmacological agent may be any agent comprising at least one of alcohol functional groups. Alcohol functional groups on the pharmacological agent will be the target for attachment to the naphthalimide compound via an ester linkage. Exemplary pharmacological agents comprising at least one alcohol functional group, include but are not limited to, paclitaxel, everolimus, sirolimus, zotarolimus, and biolimus. For example, both everolimus and sirolimus have a readily available reactive alcohol in the 40-position that is a good synthetic target for attachment. Similarly, both zotarolimus and biolimus have a readily available alcohol functional group in the 28-position.

Additional pharmacological agents that can be tethered to the compounds of the present invention include anti-thrombogenic agents, such as heparin, and magnesium sulfate; antiproliferation agents, such as paclitaxel and rapamycin; anticancer drugs; immunosuppressors; anti-infectives; anti-rheumatics; antithrombotic; HMG-CoA reductase inhibitors; CETP inhibitors ACE inhibitors; calcium antagonists; antihyperlipidemics; integrin inhibitors; antiallergics; antioxidants; GPIIbIIIa antagonists; retinoids; carotenoids; lipid-level lowering medicaments; DNA synthesis inhibitors; tyrosine kinase inhibitors; antiplatelets; antiinflammatories; tissue-derived biomaterials; interferons; monoclonal anti bodies; and NO production promoters.

Nonlimiting examples of the anticancer drugs include vincristine, vinblastine, vindesine, irinotecan, pirarubicin, doxorubicin, paclitaxel, docetaxel, mercaptopurine, and methotrexate.

Nonlimiting examples of the immunosuppressors include rapamycin and its derivatives, tacrolimus, azathioprine, cyclosporine, cyclophosphamide, mycophenolate mofetil, gusperimus, and mizoribine.

Nonlimiting examples of the anti-infectives, include antibiotics, antifungal, antiviral, antimycobacteria, antiprotozoal, antihelmintics/antiparasitic, and vaccines. Antibiotics include but are not limited to mitomycin, adriamycin, doxorubicin, actinomycin, daunorubicin, idarubicin, pirarubicin, aclarubicin, epirubicin, peplomycin, aminoglycosides, carbapenems, cephalosporins [1st-5th generation], aztreonam, fluoroquinolones, penicillins, macrolides, tetracyclines, monobactams, tigecycline, vancomycin, and zinostatin stimalamer. Antifungals include but are not limited to Amphotericin B, liposomal Amphotericin B, Lipid complex amphotericin B, flucytosine, nystatin, fluconazole, itraconazole, ketoconazole, posaconazole, voriconazole, terbinafine, caspofungin, micafungin, anidulafungin. Antivirals include but are not limited to acyclovir, adefovir, amantadine, cidofovir, entecavir, famciclovir, penciclovir, foscarnet, ganciclovir, interferon alpha, lamivudine, oseltamivir, ribavirin rimantadine, tenofovir, valacyclovir, valganciclovir, zanamivir, anti-HIV drugs. Anti-mycobacterials include but are not limited to ethambutol, isoniazid, pyrazinamide, rifabutin, rifampin, rifapentine, para-aminosalicylic acid, streptomycin, amikacin.

Nonlimiting examples of the antirheumatics include methotrexate, sodium thiomalate, penicillamine, lobenzarit, and DMARDs (disease modifying anti-rheumatic drugs, such as abatacept, adalimumab, anakinra, etanercept, tocilizumab, infliximab, rituximab, chloroquine, sulfasalazine, gold salts).

Nonlimiting examples of the antithrombotics include heparin, low molecular weight heparins (fondaparinux, enoxaparin, dalteparin), aspirin, warfarin, clopidogrel, prasugrel, ticagrelor, rivaroxaban, dipyridamole, abciximab, antithrombotic preparations, ticlopidine, and hirudin.

Nonlimiting examples of the HMG-CoA reductase inhibitors include serivastatin, serivastatin sodium, atorvastatin, nisvastatin, itavastatin, fluvastatin, fluvastatin sodium, simvastatin, rosuvastatin, and pravastatin.

Nonlimiting examples of the ACE inhibitors include quinapril, perindopril erbumine, trandolapril, cilazapril, temocapril, delapril, enalapril maleate, lisinopril, and captopril.

Nonlimiting examples of the calcium antagonists include hifedipine, nilvadipine, nicardipine, nifedipine, nimodipine, isradipine, felodipine, diltiazem, verapamil, benidipine, amlodipine, and nisoldipine.

Illustrative of the antihyperlipidemics is probucol, but may also include bile acid sequestrants, fibric acid derivatives, and statins.

Illustrative of the integrin inhibitors is AJM300.

Illustrative of the antiallergics is tranilast, but may also include antihistamines, antileukotrienes, mast cell stabilizers, decongestants, and glucocorticoids.

Nonlimiting examples of the antioxidants include catechins, anthocyanine, proanthocyanidin, lycopene, and β-carotene. Among the catechins, epigallocatechin gallate may be used.

Illustrative of the GPIIbIIIa antagonists is abciximab.

Illustrative of the retinoids is all-trans retinoic acid, but may also include Retinol, retinal, isotretinoin, alitretinoin, etretinate, acitretin, tazarotene, bexarotene, Adapalene.

Preferred examples of the flavonoids include epigallocatechin, anthocyanine, and proanthocyanidin.

Nonlimiting examples of the carotenoids include β-carotene and lycopene.

Illustrative of the lipid-level lowering medicaments is eicosapentaenoic acid including in combination with docosahexaenoic acid.

Illustrative of the DNA synthesis inhibitors are 5-FU, 6-mercaptopurine, 6-thioguanine, allopurinol, capecitabine, cytarabine, fludarabine, gemcitabine, leucovorin, methotrexate, and pemetrexed.

Nonlimiting examples of the tyrosine kinase inhibitors include imatinib, sunitinib, gefitinib, erlotinib, genistein, tyrphostin, and erbstatin.

Nonlimiting examples of the antiplatelets include ticlopidine, cilostazol, and clopidogrel.

Nonlimiting examples of the antiinflammatories include steroids such as dexamethasone and prednisolone.

Nonlimiting examples of the tissue-derived biomaterials include EGF (epidermal growth factor), VEGF (vascular endothelial growth factor), HGF (hepatocyte growth factor), PDGF (platelet derived growth factor), and BFGF (basic fibrolast growth factor).

Illustrative of the interferons is interferon-γ1a.

Illustrative of the NO production promoters is L-arginine.

As to whether one of these pharmacological agents or a combination of two or more different ones should be used, a selection can be made as needed depending on the case.

4-amino-1,8-naphthalimide compounds of the present invention can also be labeled. In an aspect, the compound is covalently bound to biotin via standard DCC coupling methods, as an example. Alternative methods for labeling a compound are known to those of ordinary skill in the art and are contemplated herein. The labeled compound will be easily detectable using a fluorescent or enzymatic assay linked to streptavidin from a streptavidin horseradish peroxidase system.

It is also possible to radiolabel the compounds of the present invention by the incorporation of labeled carbon, hydrogen, nitrogen, or oxygen during the conversion of the pharmacological agent. Any suitable radiolabel or isotopic marker known in the art can be used, such as hydrogen, carbon, pnictogens, chalcogens, and halogens, etc. However, it is to be understood that the labeled compounds of the present invention must be safe for administration to humans.

The compounds disclosed herein can be dissolved in a solvent to form a composition. In an example, the solvent can be phosphate buffered saline (PBS). Other suitable solvents include dimethylformamide and isopropyl alcohol. In certain embodiments, the composition can optionally comprise one or more excipients, buffers, carriers, stabilizers, preservatives and/or bulking agents, and is suitable for administration to a patient to achieve a desired effect or result. The composition can be in any desired form, including but not limited to a liquid, a solid, a dispersion, a suspension, a hydrogel, a particle, a nanoparticle, a thin film, and and shaped structure.

The 4-amino-1,8-naphthalimide compounds can be present in the composition in a concentration from about 0.01 mg/mL to about 100 mg/mL, for example from about 0.1 mg/mL to about 50 mg/mL, and as a further example from about 1 mg/mL to about 30 mg/mL. As a specific example, the 4-amino-1,8-naphthalimide compound is present in a composition at a concentration of 2 mg/mL.

The concentration of the compound, and optionally a tethered pharmacological agent, can be chosen such that a therapeutic effect is achieved when released into a blood vessel. One of ordinary skill in the art would readily be able to determine the concentration of the compound and/or the concentration of the pharmacological agent, in order to achieve the desired result.

The composition of the present invention may be provided in vials of various sizes for ease of use. In particular, an 8 mL vial can be used to hold 7 mL of the disclosed composition. The composition can be dispersed from the vial in one dose or is separate doses, for example a first bolus of about 4 mL, followed by a second bolus of about 0.5 to about 1.0 mL. In an aspect, a saline flush can occur between application of the first and second bolus. Additionally, the composition can be contained in a loadable cassette or a pre-loaded syringe.

It is envisioned that the plaque-softening compound and a composition comprising the compound could be stored in a freeze-dried form, which could be reconstituted with saline/PBS prior to use.

In an aspect, there is disclosed a method for using the 4-amino-1,8-naphthalimide in a treatment zone of a blood vessel, optionally comprising a plaque matrix, the method comprising applying a bolus of a composition comprising a 4-amino-1,8-naphthalimide compound to the treatment zone of the blood vessel.

The composition disclosed herein can be applied to a blood vessel. In an aspect, a treatment zone of a blood vessel, such as an artery or vein, can be isolated. In another aspect, the composition is applied in an amount sufficient to provide a high systemic concentration. The composition can be injected into the blood vessel. In an aspect, the blood vessel is the superficial femoral artery (SFA) and its collateral branches. In another aspect, the composition of the present invention is applied to an isolated section of a blood vessel for an extended period of time, such as from about 1 second to about 1 hour, for example from about 1 minute to about 30 minutes, and for example from about 1 minute to about 10 minutes. The amount of time can vary.

The compositions of the present invention can be used to soften plaque, which can improve problems associated with diabetes, and peripheral artery disease. The plaque lesions can vary in size. In an aspect, the plaque lesions range in length from about 1 to about 22 cm, for example from about 4 to about 9 cm, and as a further example about 4 to about 7 cm. The diameter of these plaque lesions can range from about 5 to about 7 mm.

In the event the plaque lesion is longer than the device used to apply the 4-amino-1,8-naphthalimide compound in a single treatment, it is envisioned that such longer plaque lesions can be treated in multiple step treatments, wherein the length of the lesion, and the length of the device to apply to the composition are factors in determining how many treatments may be needed to treat a lengthy plaque lesion.

In an aspect, the composition is delivered by a delivery system comprising an injection port and at least one balloon, such as a treatment balloon. A light fiber is in the lumen of the delivery system and is designed to deliver blue light (i.e., 457 nm, for example 450-480 nm, wavelength) at low power. The blue light activates the PEG-based composition to cross-link with biomolecules of the vessel wall, such as collagen.

Any delivery system, including catheter designs with at least one balloon, can be used to deliver the plaque-softening composition to the treatment area, e.g., blood vessel. An exemplary delivery system can be found in U.S. Provisional Application No. 61/679,591, entitled "Endovascular Multi-Balloon Catheters with Optical Diffuser for Treatment of Vascular Stenoses,", as well as U.S. Pat. No. 8,242,114, the disclosures of each which are hereby incorporated by reference. In an aspect, the distal end of a catheter can include a weeping balloon with micropores to provide a gradual infusion to the treatment site of the disclosed composition.

In particular, the vessel can be prepared by initial dilatation using angioplasty balloon to treat the stenotic region of diseased vessel (i.e., artery or vein). The composition is then injected between two occlusion balloons which isolate the treated vessel wall and bathe the vascular tissue. A secondary dilatation balloon located between the two occlusion balloons is inflated to restore the vessel lumen to the desired diameter. The blue light is delivered to "activate" the composition. The activated composition cross-links with native collagen fibers and/or covalently bonds a tethered drug to the blood vessel wall.

When activated, the naphthalimide compounds of the present invention have a singlet charge transfer state, which does not produce singlet oxygen. This is in contrast to singlet oxygen production, which is through triplet state sensitization. See Samanta, Ramachandram, Saoja, An investigation of the triplet state properties of 1,8-naphthalimides: a laser flash photolysis study, J. Photochem. Photobiol A; Chem, 101 (1996), 29-32 (and references therein). The naphthalimide compounds of the present invention decay predominately by intramolecular charge transfer state that leads to emission (C-T fluorescence). The lack of oxygen dependence of the emission of the naphthalimide compound indicates the charge transfer states are short lived.

Figure 3:
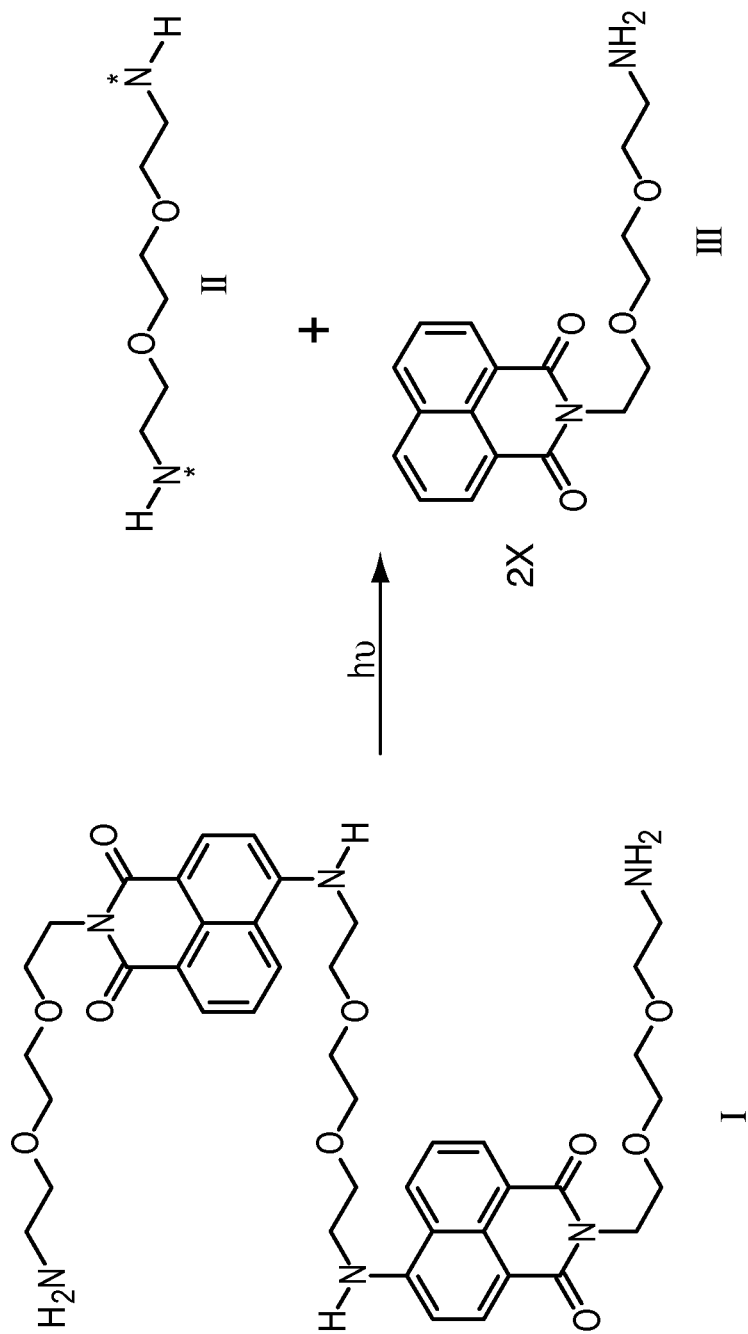
FIG. 3 illustrates a reaction scheme for the activation of a naphthalimide compound of the present invention.

The activation of the naphthalimide compound of the present invention is believed to follow the reaction scheme in FIG. 3. As illustrated in the reaction scheme, an exemplary dimer compound (I) is activated. The "linker" functional group (II) is released as well as two compounds (III). It is believed without being limited to any particular theory, that these reaction products (II) and (III) enter the systemic circulation and is excreted by the kidneys.

Fluorescence studies can be used to demonstrate that the composition comprising the disclosed naphthalimide compound can penetrate the blood vessel, and thus treatment over the entire area of the blood vessel can be ensured.

There is disclosed herein a kit of parts for use in restoring vascular compliance comprising: a composition comprising a 4-amino-1,8-naphthalimide; a delivery system for delivery of the composition into a blood vessel; and an activating agent for activating the composition after the composition has been applied to the blood vessel.

There is also disclosed a method of restoring vascular compliance in a diseased blood vessel, comprising: inserting a delivery system into the blood vessel; applying a bolus of a composition comprising a 4-amino-1,8-naphthalimide compound to the blood vessel; activating the composition with a sufficient amount of an activating agent to restore the vascular compliance of the blood vessel. The blood vessel can be an artery or a vein. The vascular compliance of the blood vessel is restored to its native compliance within about 90 to about 120 days after the activating step Prior to application of the composition, the diseased blood vessel does not exhibit native vascular compliance as a result of atherosclerosis, a surgical procedure, diabetes, hypertension, autoimmune disease, aneurysm, accident or injury, a minimally-invasive intervention procedure, and repeated access by needle. The surgical procedure can be at least one of an endarterectomy, vascular graft implant, vascular anastomosis, and bypass graft. The minimally-invasive interventional procedure comprises at least one of PTA, PTCA, vascular stenting and atherectomy.

As a result of the activating step disclosed in the method above, the blood vessel retains its luminal gain from the insertion step without a stent, wherein the stent is chosen from permanent stents and resorbable stents.

The method may further comprise, prior to insertion of the delivery system, a step of applying an initial bolus of a composition comprising a 4-amino-1,8-naphthalmide compound to the blood vessel in order to soften plaque present in the blood vessel.

There is also disclosed a method of inhibiting smooth muscle cell proliferation in a diseased blood vessel, comprising: performing an interventional procedure on the diseased blood vessel that initiates smooth muscle cell proliferation in the diseased blood vessel; and applying a bolus of a composition comprising a 4-amino-1,8-naphthalimide compound to the diseased blood vessel; wherein the application of the composition inhibits the smooth muscle cell proliferation in the diseased blood vessel.

The interventional procedure can be selected from the group consisting of repeated access by needle, endarterectomy, vascular graft implant, vascular anastomosis, bypass graft, PTA, PTCA, vascular stenting and atherectomy.

Due to the disclosed method, there is an increase in at least one of NO production, tissue plasminogen activators, and thrombomodulin.

There is also disclosed a method of restoring vascular compliance of a blood vessel, comprising: performing an interventional procedure on the diseased blood vessel that initiates smooth muscle cell proliferation in the diseased blood vessel; and applying a bolus of a composition comprising a 4-amino-1,8-naphthalimide compound to the diseased blood vessel in an amount sufficient for the composition to reach an immediate area of the diseased blood vessel where the interventional procedure was performed as well as the surrounding areas; wherein the application of the composition to the immediate and surrounding areas of the interventional procedure restores the vascular compliance without exhibiting any areas of mismatched vascular compliance. In an aspect, the immediate area of the diseased blood vessel wherein the interventional procedure was performed retains a vascular compliance which is approximately equal to the vascular compliance of the surrounding areas.

Further, there is disclosed a method of acutely restoring vessel compliance to a level approaching normal limits, comprising performing a revascularization procedure on the vascular treatment site; applying a bolus of a composition comprising a 4-amino-1,8-naphthalimide compound to the vascular treatment site in an amount such that the vascular treatment site immediately re-establishes a vasomotion function to accommodate pulsatile blood flow, while retaining the luminal gain achieved during the revascularization procedure; wherein the vessel compliance of the vascular treatment site is acutely restored to a level approaching normal limits. In an aspect, the restoration of vessel compliance occurs immediately after the revascularization procedure.

A method for maintaining luminal gain of a diseased blood vessel, comprising: increasing a luminal gain of a diseased blood vessel using a dilatation device; applying a composition comprising a 4-amino-1,8-naphthalimide compound to the diseased blood vessel having an increased luminal gain; activating a composition with an activating agent to release polyether functional groups; reinforcing a wall of the diseased blood vessel with the released polyether functional groups; wherein the reinforced wall retains the luminal gain without compromising the vascular compliance of the diseased blood vessel.

EXAMPLES

Example 1—Synthesis and Initial Purification of a Compound of Formula (V)

In a 100 mL round bottom flask, 15 grams of JEFFAMINE® 148 (Sigma-Aldrich, St. Louis, Mo.) was combined with 1 gram of 4-bromo-1,8-naphthalic anhydride (Sigma-Aldrich, St. Louis, Mo.). The temperature was held from about 100 to about 110° C. for about 18 to about 24 hours, and was constantly stirred. The reaction mixture was cooled to room temperature, combined with 50 mL of ethanol (Pharmco-Aaper, Brookfield, Conn.), and then refrigerated at about 4° C. until crystals precipitated from solution (approximately 48 hours). The cold solution was then filtered by vacuum filtration, and the product, crystals of the compound of formula (V), were washed with 10 mL of cold ethanol. The percent yield after precipitation with ethanol was calculated to be 25%.

Purification of the crystals involved combining the isolated product with 30 mL of ethanol and heating the mixture to boiling. When all of the crystals were dissolved, the heat was removed and the solution cooled to room temperature, then refrigerated to about 4° C. overnight, allowing crystals to precipitate from solution. The crystals were isolated using vacuum filtration, rinsed with 10 mL of cold ethanol, and allowed to air dry. No significant losses were recorded during this recrystallization step. The material prepared in this fashion was approximately 75% pure naphthalimide dimer, the desired product, with the impurity profile composed of monomeric analogues.

Example 2—Preparation of the Compound of Formula (V) Standard Solution

The naphthalimide solution was prepared as described in Example 1. A 5.0 mg/mL solution was prepared by diluting the compound of formula (V) with phosphate-buffered saline (PBS). With constant stirring, the sample pH was adjusted to 7.4 by dropwise addition of a 10% (v/v) solution of acetic acid. The final concentration of the solution was confirmed by spectrophotometric analysis (Ocean Optics, USB4000), in which the absorbance (440 nm) of a 1:200 dilution of the compound of formula (V) solution in isopropyl alcohol was measured. The observed absorbance of this sample was 0.5.

Example 3—Naphthalimide Purity by HPLC

A chromatographic separation was performed on a modular HPLC system with a PDA detector and data analysis package (Varian), and detection wavelengths of 210, 254, 360, and 440 nm, The analytical separation was achieved using $C_{18}$ column (Alltima HP, 5 µm, 4.6×250 nm, Alltech) and gradient elution. The elution solvents consisted of mobile phase A, 0.15 (v/v) TFA (aq), and mobile phase B, a 90:10 ACN:water with 0.1% (v/v) TFA. A 1:5 dilution (PBS) of the compound of formula (V) naphthalimide standard solution from Example 2 was analyzed. Using a 204 injection volume and a flow rate of 1.0 mL/min the standard solution was introduced onto a column that had been pre-equilibrated for 10 minutes with a 95:5 mobile phase ratio of solvents A and B, respectively. Subsequent elution of the analytes was accomplished using a linear gradient with a 1 minute hold at the beginning to 90% mobile phase B at 20 minutes, followed by a 5 minute hold at the end of the gradient.

Example 4—Residual Amine Determination by HPLC Analysis

20 µL of the naphthalimide solution from Example 2 was placed in a micro-centrifuge tube and diluted with 180 µL of reaction buffer (0.15 M $NaHCO_3$, pH=8.6). The sample was vortex mixed and then 200 µL of the dabsyl chloride reagent (12.4 mM DABS-Cl in acetone) was added. The samples were incubated at 70° C. for 15 minutes with intermittent vortex mixing, and then cooled in an ice bath for 5 minutes. Next, 400 µL of a dilution buffer (50:25:25 (v/v/v) acetonitrile:ethanol:mobile phase A (chromatographic mobile phase)) was added and the sample mixed. Samples were then centrifuged at 10,000 rpm (Eppendorf 541R) for 5 minutes and then analyzed.

The chromatographic separation was performed on a modular HPLC system with a PDA detector (436 mm) and data analysis package (Varian). The analytical separation was achieved using $C_{18}$ column (Alltima HP, 5 µm, 4.6×250 mm, Alltech) and gradient elution. The elution solvents consisted for mobile phase A, 96% 9 mM $Na_2HPO_4$, 4% DMF and 0.1% TEA (aq.), and mobile phase B, 80:20 ACN:water. A 20 µL injection volume and flow rate of 1.0 mL/min were used with a starting mobile phase ratio of 92:8 mobile phase A to B, respectively, a two minute hold, and then a gradient to 100% mobile phase B at 40 minutes followed by a 10 minute hold. JEFFAMINE® 148 standards were prepared and used to determine linearity and limit of detection for the compound of formula (V) standard solution.

Example 5—Isolation and Purification of a Compound of Formula (V) Using Preparative HPLC A preparative HPLC approach was used to isolate and specifically purify the compound of formula (V) dimer from the compound of formula (V) naphthalimide product produced from the ethanol crystallization. The HPLC method used was based on the purity method outlined above; however, method modifications were made to replace acetonitrile with ethanol and TFA with acetic acid in the mobile phase. The preparative separation utilized a $C_{18}$ column (X-bridge, 10 µm, 19×250 mm, Waters). The mobile phase consisted of mobile phase A, 0.1% acetic acid (aq), and mobile phase B, 9:1 ethanol:water (0.1% v/v acetic acid). The column was pre-equilibrated at a starting mobile phase of 95% A:5% B for 20 minutes, at the start of the gradient was a 2 minute hold followed by a linear gradient to 90% B at 40 minutes and a 10 minute hold. An injection volume of 8.5 mL (12 mg/mL purified compound of formula (V)) and flow rate of 8.5 mL/minute were used as well as a detector wavelength of 440 nm. The compound of formula (V) fractions were collected and analyzed using the analytical purity method presented above. Fractions meeting a minimum purity criterion were combined and the solvent driven off by rotovapping the solution to dryness. Excess acetic acid was removed by repeated (two total) dissolution of the product in deionized water followed by rotovapping to dryness. Finally the product was quantitatively transferred from the round bottom flask to a freeze drying flask by dissolving the product in a minimal amount of deionized water. This solution was frozen at a temperature of −80° C. for a minimum of 24 hours. This final purification approach effectively removed excess solvent and acetic acid from the product as a dimer solution at the desired pH value of 7.4. The naphthalimide dimer solution has demonstrated excellent stability for periods up to one year. The dimer in powder form has shown no evidence of degradation for periods exceeding one year of storage in a dessicator at room temperature.

Example 6—Spectral Characterization of the Naphthalimide Monomer and Dimer

Standards of the naphthalimide monomer and dimer were analyzed by ESI-MS analysis for molecular weight (MW) confirmation. Standards were analyzed on a Waters A-TOF I mass spectrometer. A stock solution of the purified solid was prepared in PBS at a concentration of 2 mg/mL. Serial dilution was used to prepare solutions of decreasing concentration until the limit of detection was reached. Absorbance ($\lambda_{max}$) curves were measured for the naphthalimide dimer using PBS, DMF, and IPA as the dilution solvent. The extinction coefficient for the naphthalimide monomer was only determined in IPA.

In view of the foregoing, one of ordinary skill in the art would be able to synthesize the disclosed monomer, dimer, trimer (star, capped, linear) naphthalimide compounds disclosed herein.

Example 7—Plaque Penetration

Diseased arteries were obtained from limb amputations (leg) due to advanced Periperal Arterial Disease (PAD) from patients at Avera McKennan hospital. The received arteries were evaluated and chosen such that the diseased section was of reasonable size to accommodate the treatment catheter balloon length being used. The catheter balloon diameter used was also matched to the diameter of the artery and capable of achieving a 1:1.25 (ratio of artery diameter to balloon diameter) overstretch. The artery was laid in a petri dish and an angioplasty balloon was inserted and inflated for 60 seconds to impart the desired overstretch. While the angioplasty balloon was inflated a permanent marker was used to define the treatment zone (where the overstretch was imparted by the balloon) on the outer surface of the artery. The angioplasty balloon was deflated and removed. The inner lumen of the diseased artery was exposed to a plaque softening composition comprising a compound of formula (V) naphthalimide formulation (2 mg/mL in phosphate buffered saline, pH=7.4) for a period of 5 minutes. For the purpose of filling the artery, one end was clamped, the artery was held upright and a syringe was used to dispense the naphthalimide solution until the inner lumen was filled. The open end of the artery was then clamped and the soaking period of 5 minutes commenced. After the 5 minute soaking period, the clamps were removed and a treatment catheter with a dilatation balloon and capable of housing a light fiber for light activation was centered in the treatment zone of the artery as defined by the markings made on the outside of the artery. The treatment balloon was inflated to a similar diameter as the angioplasty balloon in the previous step and light activation was imparted using the light fiber contained in the central lumen of the catheter and illuminating through the treatment balloon. Light activation involved using a laser (447 nm) and a power level of 625 mW/cm delivered to the treatment zone for a period of 60 seconds. After completion of light activation, the laser was turned off, the treatment zone balloon was deflated and the catheter removed from the artery. Control arteries having no exposure to the plaque softening compound were treated in an identical manner to those receiving the plaque softening compound, however, phosphate buffered saline (pH 7.4) was used in place of the plaque softening compound, i.e., the naphthalimide compound. Arteries were cut open lengthwise and the treated section was evaluated by visual examination.

Figure 4A:
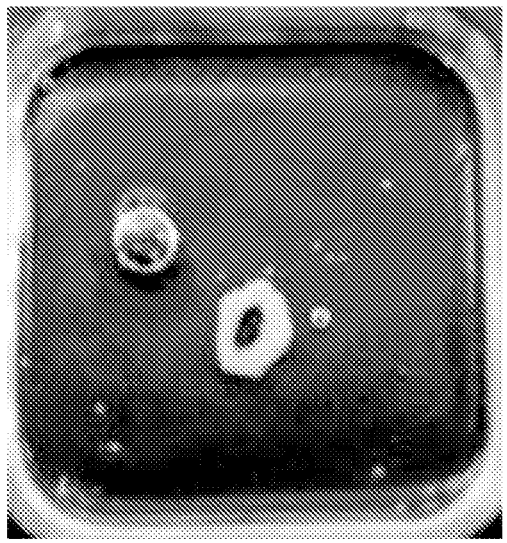
FIGS. 4a-f are photos illustrating various aspects of the present invention.
Figure 4B:
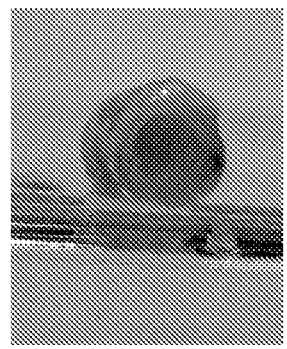
Figure 4C:
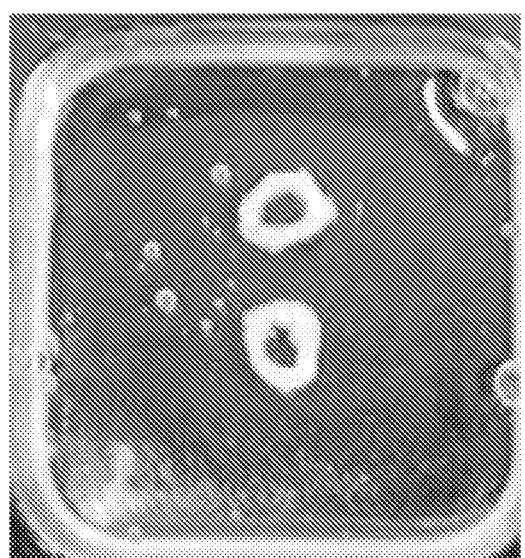
Figure 4D:
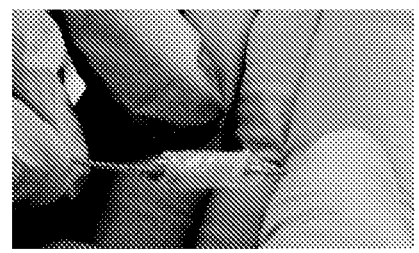
Figure 4E:
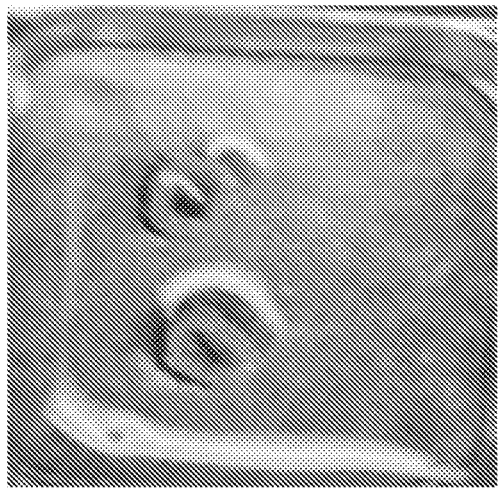
Figure 4F:

FIGS. 4a and 4b are photos of an untreated section of popliteal artery that was fairly healthy, having only a slight plaque formation. FIGS. 4c and d are photos of the same artery after angioplasty with a 25% overstretch. FIGS. 4e and f are photos of the same artery after it has been treated, i.e., soaked with the plaque softening composition comprising the compound of formula (V).

Figure 5A:
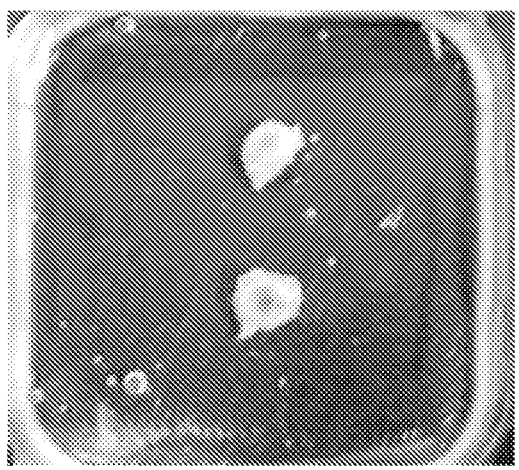
FIGS. 5a-f are photos illustrating various aspects of the present invention.
Figure 5B:
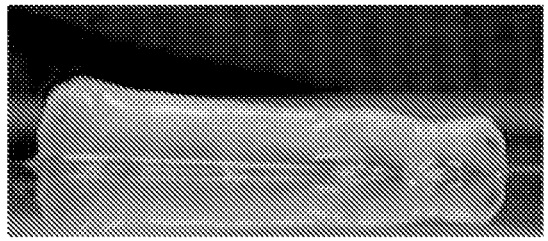
Figure 5C:
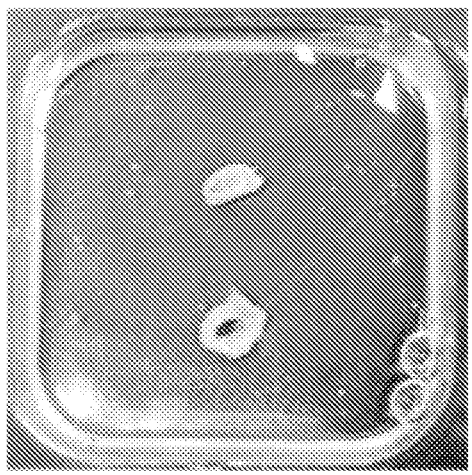
Figure 5D:
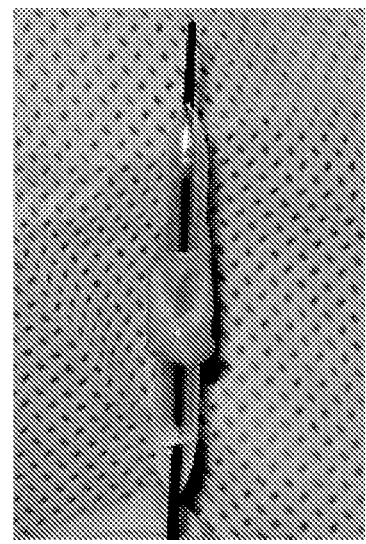
Figure 5E:
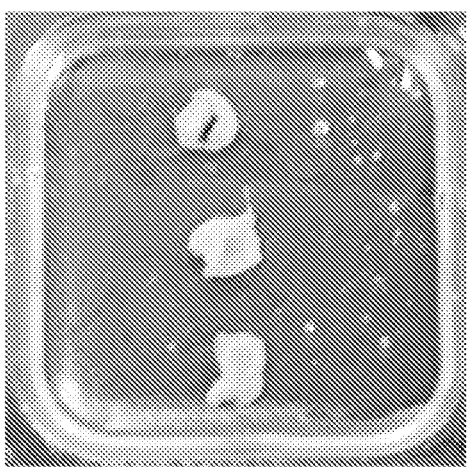
Figure 5F:
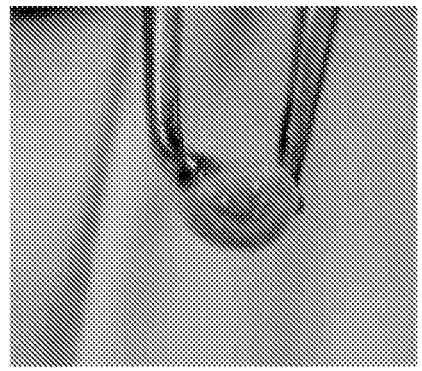

FIGS. 5a and 5b are photos of an untreated section of tibial artery that was partially covered in hard or soft plaque. FIGS. 5c and d are photos of the same artery after angioplasty with a 37% overstretch. FIGS. 5e and f are photos of the same artery after it has been treated, i.e., soaked with the plaque softening composition comprising the compound of formula (V).

Figure 6A:
FIGS. 6a-f are photos illustrating various aspects of the present invention.
Figure 6B:
Figure 6C:
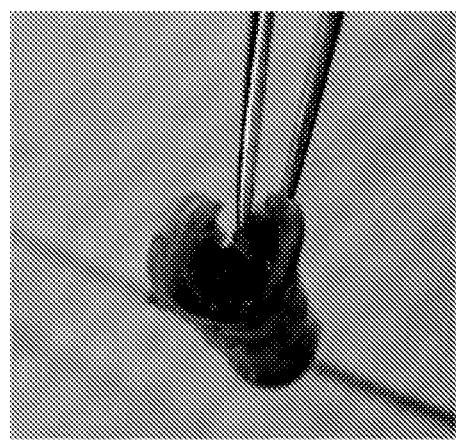
Figure 6D:
Figure 6E:
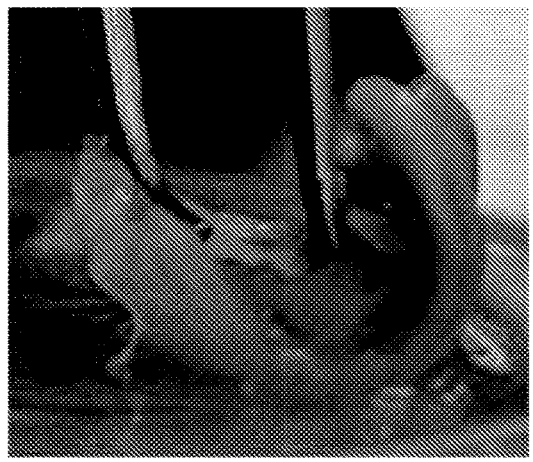
Figure 6F:
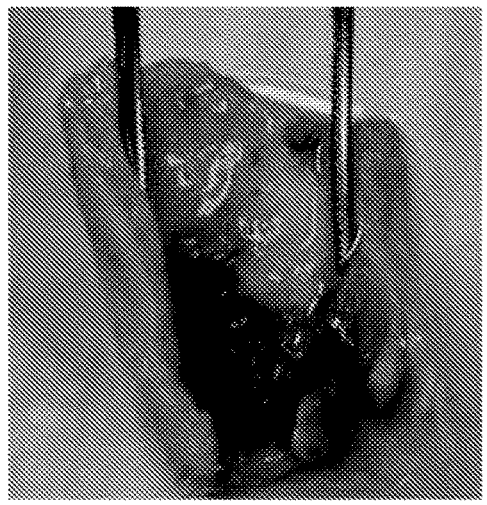

FIGS. 6a, 6b, and 6c are photos of an untreated section of popliteal artery that was partially covered in hard or soft plaque. As can be seen in FIG. 6b the artery was cut open lengthwise (no angioplasty). FIGS. 6d, 6e and 6f are photos of the same artery after it has been treated, i.e., soaked with the plaque softening composition comprising the compound of formula (V).

Figure 7A:
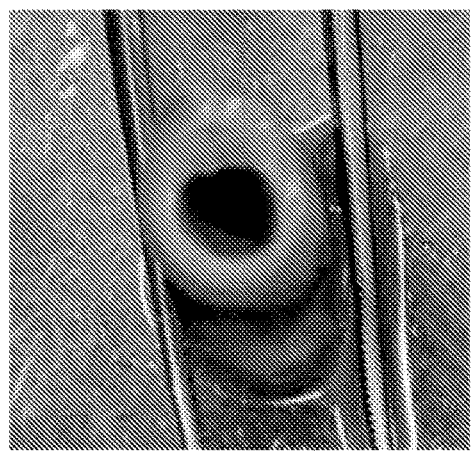
FIGS. 7a-e are photos illustrating various aspects of the present invention.
Figure 7B:
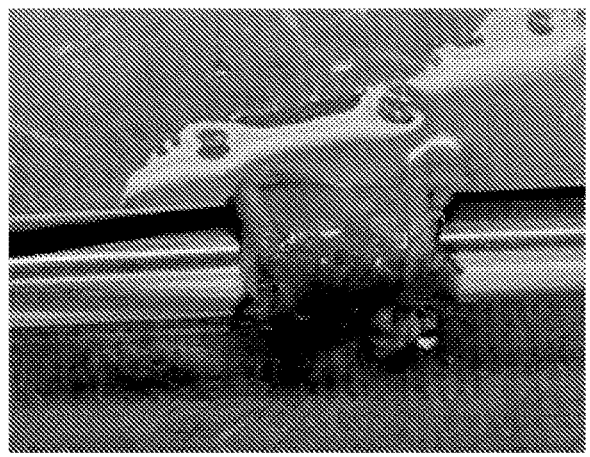
Figure 7C:
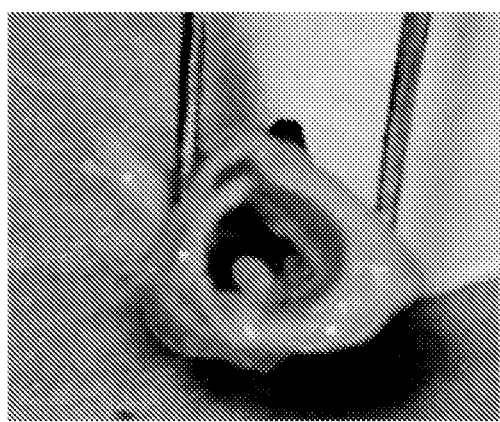
Figure 7D:
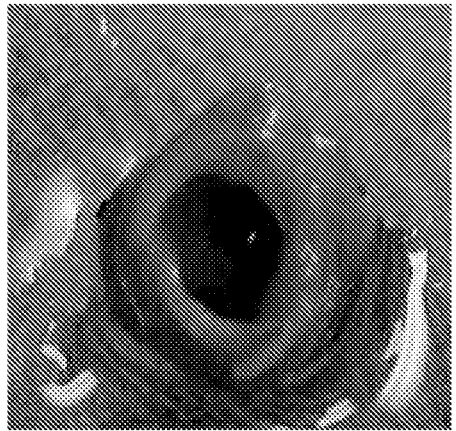
Figure 7E:

FIG. 7a is a photo of a section of popliteal artery having large areas of soft plaque. FIGS. 7b and 7c are photos of the same artery after angioplasty with a 25% overstretch. FIGS. 7d and 7e are photos of the same artery after it has been treated, i.e., soaked with the plaque softening composition comprising the compound of formula (V).

Figure 8:
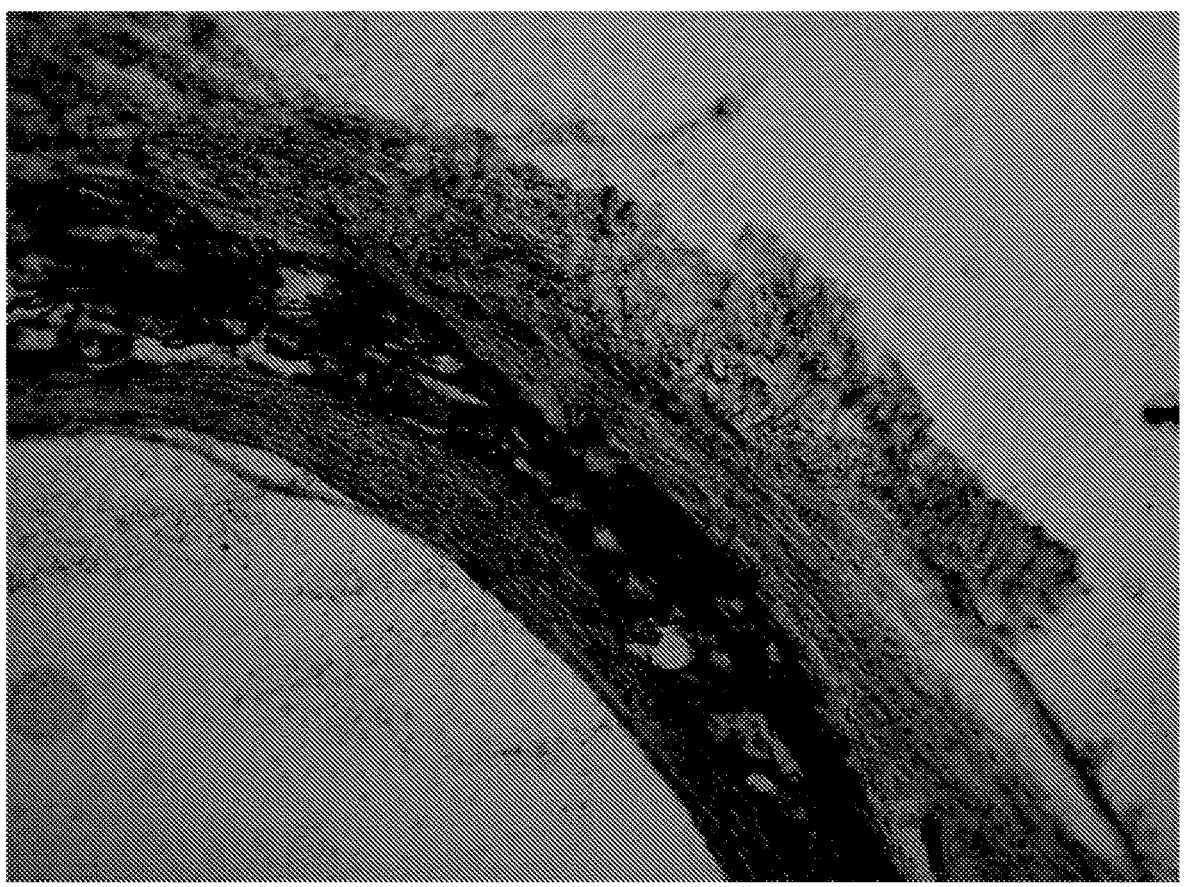
FIG. 8 is an image captured on a microscope showing the various layers of a blood vessel and the crystalline plaque (black cells) located between the two media layers of tissue.

Prior to cutting the artery for visual examination samples from the treated and untreated sections were collected and preserved for histological examination. This sample preparation involved using surgical scissors to cut a section of approximately 2 mm in length and placing the section into OCT embedding medium in a plastic mold. The sample was then immediately immersed in liquid nitrogen for a period of at least 1 hour. After this time, samples were stored in a −80° C. freezer until ready for further analysis. Histological analysis involved placing the frozen section into a cryostat and cutting into sections of 10 microns in thickness. Individual sections were placed onto poly-L-lysine coated glass slide, coverslipped from frozen using Cytoseal 60 and viewed under dark field magnification (10×) using a Zeiss Axiovert 200 microscope. Additional histological evaluation was performed using H&E staining which allowed for better elucidation of the soft plaque. The crystalline nature of hard plaque is readily visible without staining. Under this magnification the crystalline structure of the calcific plaque was readily visible, as shown in FIG. 8 the dark area between the two lighter colored areas of the media. Specific landmarks, such as the presence and appearance of both hard (calcified) and soft plaque, were identified. There was a definitive visual observation of apparent softened plaque in the treated region. There was a definitive observation of tacking of intimal flaps.

Figure 9A:
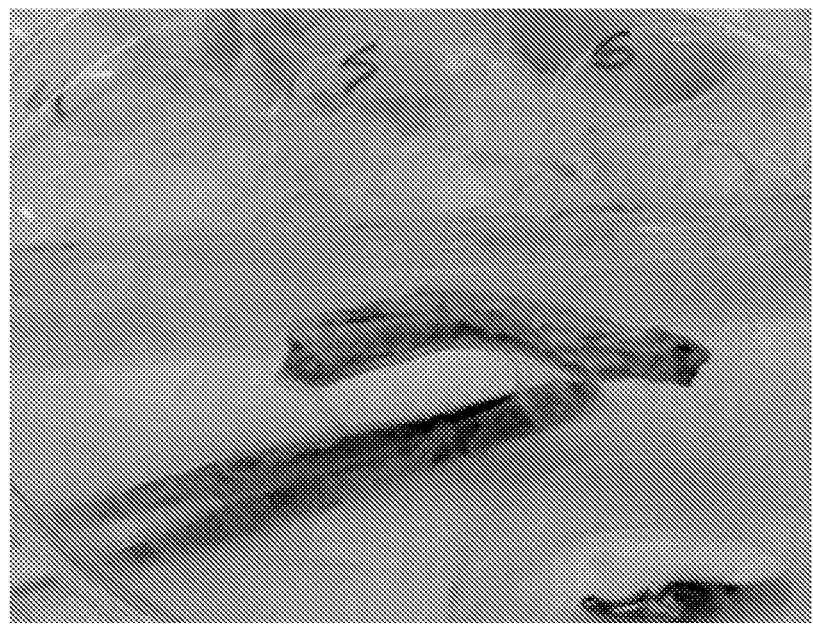
FIGS. 9a and 9b are photos of an isolated section of a blood vessel before and after it has been subjected to a plaque-softening compound of the present invention.
Figure 9B:
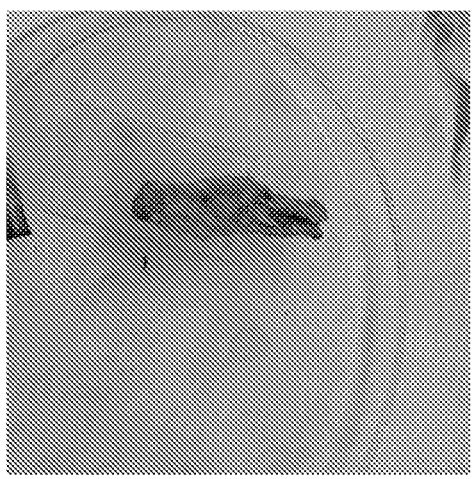
Figure 10:
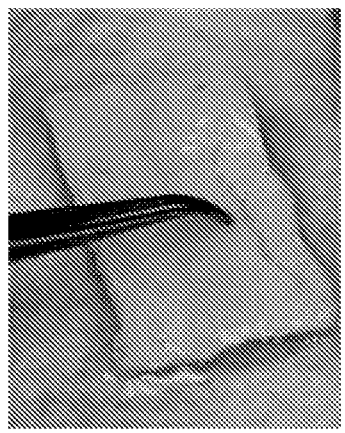
FIG. 10 is a photo of an untreated section of a blood vessel after angioplasty and exhibiting a tissue dissection or fissure.

Microscopic Evaluation—In particular, the treated plaque looked and felt softer and creamier. See FIGS. 9a-b. FIG. 9a is a photo of an isolated section of a blood vessel comprising a plaque matrix. The shriveled nature of the artery represents what the untreated section of the artery looked like after the artery was cut open. FIG. 9b is a photo is the blood vessel of FIG. 9a after it has been subjected to application of composition comprising a plaque-softening compound. The treated section is distinguishable from the untreated portion of the artery as it is distended and smoother. The appearance of the untreated portion (to the right) is very similar to the shriveled nature of the entire artery as shown in FIG. 10a. The treated and untreated sections of artery were viewed under a microscope. There was less evidence of calcium crystals in the treated sections.

Example 8—Tissue Immersion

A sample of human tissue from the common and lower femoral artery was received. It was stored in saline and refrigerated until use. Based upon visual and tactile observations, the arteries were approximately 7-8 mm in diameter and contained evidence of both hard and soft plaque. The soft plaque has a yellow fatty appearance that is distinguishable from the vessel wall. The hard plaque presents itself as hard pieces of material that can be pulled (with a forceps) from the soft plaque. Sections of the artery suitable for catheter work were segregated and stored in phosphate buffered saline (PBS), pH=7.4. From the remaining arterial sections, pieces of tissue containing both hard and soft plaque were removed. These pieces were either placed in a solution of PBS (pH=7.4), or dimeric naphthalimide, such as a compound of formula (V) (which is in PBS, pH=7.4). Prior to immersion in either solution the relative hardness of the plaque was evaluated via manual manipulation with a forcep. After a 5 minute soak in solution (typical exposure time), no difference in the samples soaked in PBS was noticed (control). There was a slight softening of the plaque exposed to a compound of formula (V) (inventive example). The samples were then left in their respective solutions for an additional 90 minutes. The plaques soaking in the PBS (control) remained hard, whereas the plaques soaking in the compound of formula (V) (inventive example) were significantly softer and more pliable.

Example 9—Tissue Receiving Only Angioplasty

The tissue was an artery approximately 7.4 mm in diameter. An Ultra-thin SDS 8 mm×30 mm catheter was used to dilate the artery to 7.55 mm (approximately a 2% overstretch). A fissure or a possible dissection running down the length of the tissue sample was observed. See FIG. 10

Figure 11A:
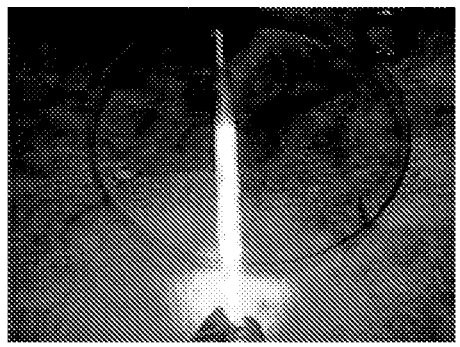
FIG. 11a is a photo of a section of artery being activated.
Figure 11B:
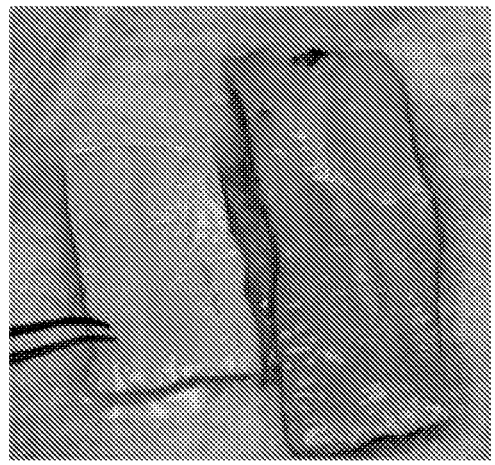
FIG. 11b is a photo of a side-by-side comparison of an untreated section of a blood vessel (on the left) with a treated section of a blood vessel (on the right).

Example 10—Tissue Receiving a Plaque-Softening Composition Comprising a Compound of Formula (V) and then Angioplasty A section (6.5 cm in length) of artery was exposed to the composition for 5 minutes. An 80 mm catheter was used to impart a 2% overstretch to the artery. The angioplasty was followed by photoactivation at 1800 mW for 60 seconds using the same 80 mm catheter with a 60 mm light fiber centered in the catheter. See FIG. 11a. When this artery was opened up there was no fissure observed as with the previous artery, however, there did appear to be somewhat of a seam which may indicate the photoactivated repair of a fissure after the plaque is pre-softened and then dilated. See FIG. 11b.

Example 11—Tissue Receiving Angioplasty and then a Plaque-Softening Composition Comprising a Compound of Formula (V)

Figure 12:
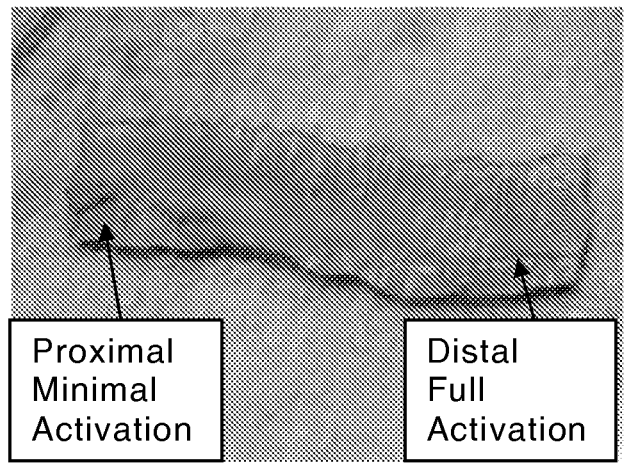
FIG. 12 is a photo of a treated section of blood vessel after activation of a plague-softening compound.

A catheter with an 80 mm treatment zone balloon was used however the photoactivating light fiber was only 60 mm in length. During activation it was noted that the light fiber was shifted distally in the catheter. This meant that the distal end of the artery was receiving photoactivation, however, the proximal end received little or no light. A fissure down the length of the artery was again observed. At the proximal end where there was minimal light activation there did not appear to be repair. Distally down the artery towards adequate photoactivation there appeared to be a seam indicating repair. At the very distal end there was a small flap which indicated that full repair may not have occurred. See FIG. 12.

Example 12—Other Photoactivated Material

Figure 13:
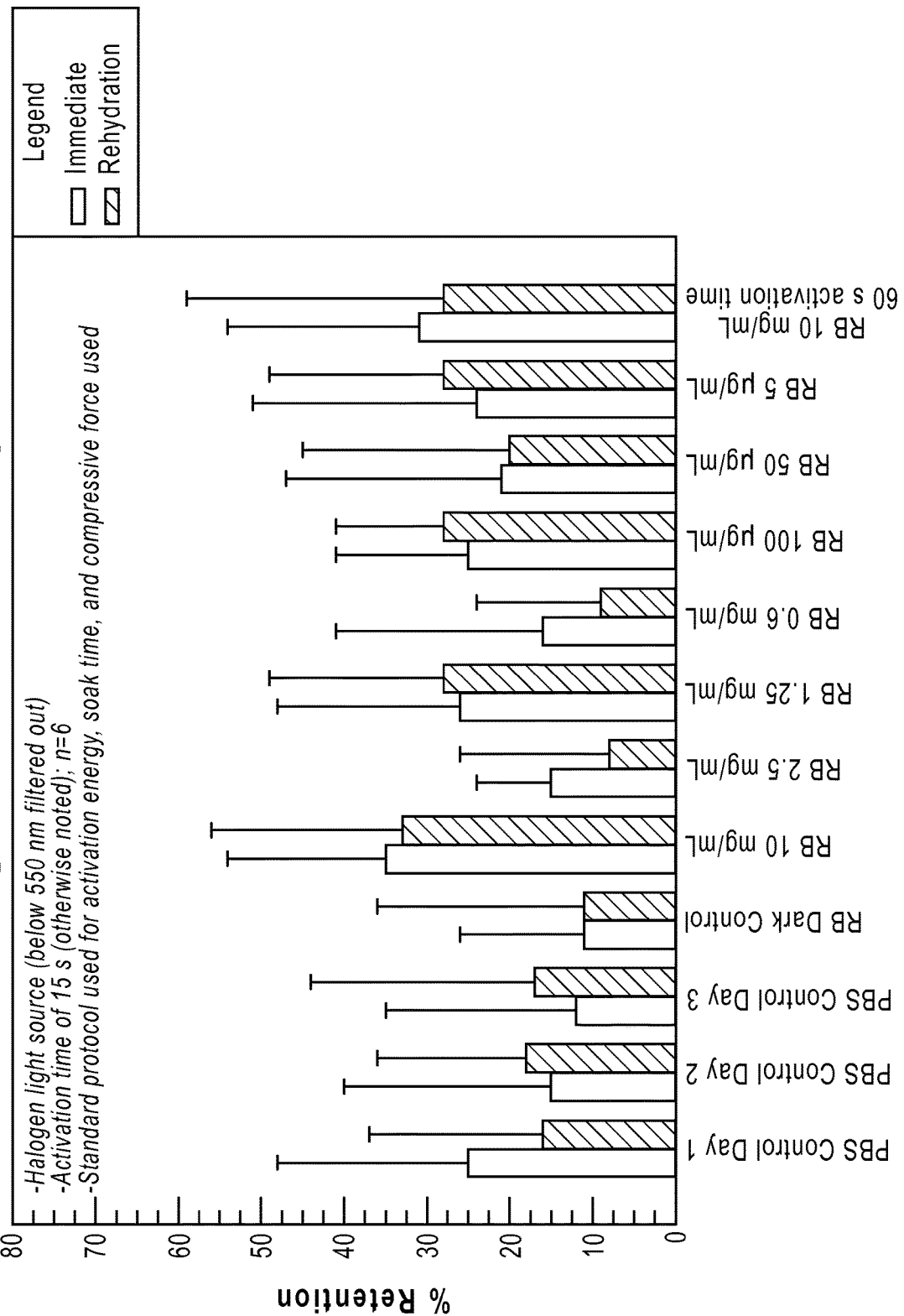
FIG. 13 is a graph illustrating arterial compression data for rose Bengal.

Singlet oxygen generating species, such as Rose Bengal, riboflavin, and methylene blue were tested to determine if they would be effective at arterial compression. No efficacy was observed, as shown in FIG. 13.

Example 13—Attachment and Release of Pharmacological Agent Tethered to a Compound of Interest A fresh excised porcine artery can be cleaned of excess tissue and rinsed in PBS. The artery wall can undergo angioplasty to simulate clinical injury. The artery can be filled with a 1.0 mg/mL solution of a pharmacological agent bound to a compound of interest, such as a naphthalimide compound, and allowed to soak for 5 minutes. A balloon catheter capable of accommodating a cylindrically illuminating fiber can be inflated in the artery to expel any extra material. The artery can be irradiated to activate the naphthalimide compound and effect the attachment of the pharmacological agent to the blood vessel wall. After irradiation, the balloon will be deflated and removed. Arterial material outside of the treatment zone, that material not around the illumination zone will be removed and discarded. The artery will be rinsed with PBS and then soaked in PBS multiple times in the dark for at least 1 hour to remove any unbound material.

To determine the attachment of the pharmacological agent to the blood vessel, the artery can be blotted dry and weighed. The artery will be homogenized and warmed to 40° C. in a basic (high pH) solution. This basic treatment will result in the rapid hydrolysis of the bond, e.g., an ester bond, and the complete release of the pharmacological agent, e.g., Everolimus. The total amount of the tethered pharmacological agent can be determined by HPLC.

To determine the release (hydrolysis) rate, a section of treated artery can be blotted dry and weighted. The artery will be placed in PBS and incubated at 37° C. Aliquots of buffer can be removed and analyzed via HPLC to determine the amount of pharmacological agent released as a function of time.

Example 14—A Proposed Synthesis of a Capped Naphthalimide Trimer

Dissolve 0.500 gram of 4-chloro-1,8-naphthalic anhydride (2.16 mmoles, mw=232) in 100 ml of anhydrous ethanol. Add 7.3 mg TEA (0.072 mmoles, mw=101). Add 0.316 grams of JEFFAMINE® T-403 (0.718 mmoles, mw=440) and protect the reaction vessel with a drying tube. (Note: The reaction produces water, the reaction may be facilitated by the addition of 20 grams of dry molecular sieves.) The reaction should be heated to 50° C. The reaction should be monitored by TLC on fluorescence plates. The product should NOT be fluorescent when viewed under blue (450 nm) light. The reaction will be run for up to 168 hours, if the reaction is not complete at this time, the solution will be verified to be basic (add TEA as necessary). If basic, the reaction temperature will be increased in 10° C. step up to reflux. Chromatography was on silica gel may be used to purify the product, the solvent system to be determined by TLC.

Dissolve 0.53 grams (0.5 mmoles, mw=1065.45) of the 4-chloro-⅓T403-naphthalimide in 1000 ml of o-dichlorobenzene (bp=178-180° C.). After the maphthalimide is completely dissolved, add 0.22 grams of JEFFAMINE®T-403 (0.5 mmoles, mw=440). The reaction will be refluxed in the dark under nitrogen and the reaction monitored by the increase in fluorescence and TLC for up to 168 hours. Partially reacted material will be fluorescent but will be not move from the origin on TLC. While the large volume of solvent has been selected to prevent formation of higher order aggregates, it will slow the reaction unacceptably. If the reaction is too slow, the volume of solvent may be reduced.

Example 15—Synthesis of 4-chloro-butyl naphthalimide

Dissolve 0.500 gram of 4-chloro-1,8-naphthalic anhydride (2.16 mmoles, mw=232) with 100 ml of anhydrous ethanol in a 250 ml round bottom flask. Add 0.22 g TEA (2.2 mmoles, mw=101). Place a small stir bar in the flask. Add a cooled reflux condenser to the flask. Place the flask in a heating mantel on a stir plate and heat to reflux. The 4-chloro-1,8-naphthalic anhydride should dissolve. After the 4-chloro-1,8-naphthalic anhydride has dissolved, add 0.16 g butyl amine (2.2 mmoles, mw=73.14) For ease of handling, add 0.2 ml of butyl amine directly through the reflux condenser. Allow the reaction to reflux for 12-24 hours. Allow the reaction mixture to cool to room temperature. The reaction can sit until your next day in the lab. Determine the extent of the reaction by TLC on normal phase TLC with 50:50 hexane:ethyl acetate as the solvent system. The product should NOT be fluorescent when viewed under blue (450 nm) light.

Example 16—Addition of Trimeric Jeffamine T-403 to the Reaction Mixture of Example 15

Return the reaction mixture to reflux. Add 0.316 grams of Jeffamine T-403 (0.72 mmoles, mw=440) directly through the condenser. Add 0.22 g TEA (2.2 mmoles, mw=101) directly through the condenser. Allow the reaction to reflux for 48-72 hours. Allow the reaction mixture to cool to room temperature. The reaction can sit until your next day in the lab. If crystals or oil forms, collect by filtration or decanting.

If there is no apparent product, add 100 ml of water and cool at 4° C. to bring the product out of solution.

Example 17—Characterization of Product from Example 16

Estimate the purity by TLC on normal phase TLC with 50:50 hexane:ethyl acetate as the solvent system. The product should be fluorescent when viewed under blue (450 nm) light.

Estimate the aqueous solubility by adding small aliquots of product to 10 ml of PBS with vigorous stirring. When the solution appears to be saturated and in equilibrium with solid product (or oil), continue to stir for 30 minutes. Then allow to settle for 30 minutes and then measure the absorbance at 440 nm. Make serial 1:10 dilutions in PBS if the measured absorbance is above 1.

| Dilution | $A_{440}$ | ~Concentration at $A_{440}$ = 1 |
|---|---|---|
| None | | 0.027 mM |
| 1:10 | | 0.27 mM |
| 1:100 | | 2.7 mM |
| 1:1000 | | 27 mM |

$$\text{Concentration} = \frac{A_{440}}{36.000 \ M^{-1}\text{cm}^{-1}} * \text{Dilution (Wild guess for } \varepsilon\text{)}$$

If the product displays reasonable solubility (>0.05 mM) test for efficacy using the gain model.

Example 18—Synthesis of EDR-148 Terminated Head Linked T-403 Trimer

Dissolve 0.500 gram of 4-chloro-1,8-naphthalic anhydride (2.16 mmoles, mw=232) with 100 ml of anhydrous ethanol in a 250 ml round bottom flask. Add 0.44 g TEA (4.4

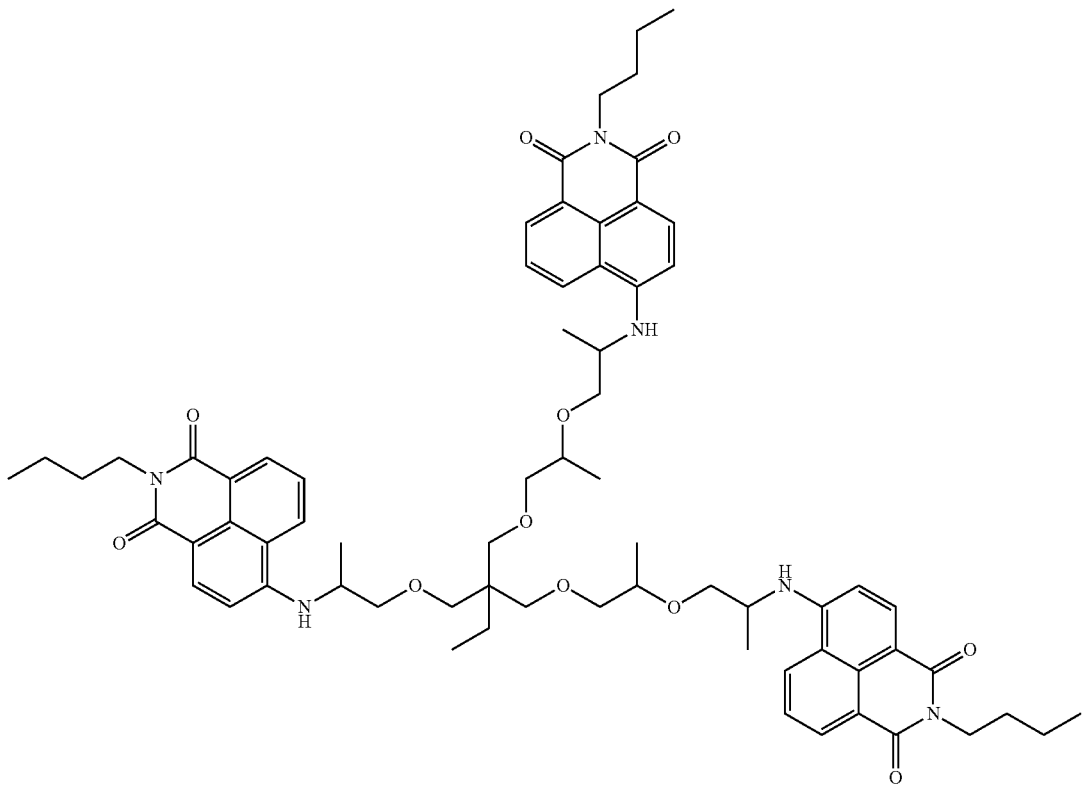 [SMILES: CCCCN1C(=O)c2cccc3c(NC(C)COCC(CC)(COCC(C)OCC(C)Nc4ccc5c6c(cccc46)C(=O)N(CCCC)C5=O)COCC(C)OCC(C)Nc4ccc5c6c(cccc46)C(=O)N(CCCC)C5=O)ccc(c23)C1=O]

mmoles, mw=101). Place a small stir bar in the flask. Add a cooled reflux condenser to the flask. Place the flask in a heating mantel on a stir plate and heat to reflux. The 4-chloro-1,8-naphthalic anhydride should dissolve. After the 4-chloro-1,8-naphthalic anhydride has dissolved, add 0.326 grams of JEFFAMINE® EDR-148 (2.2 mmoles, mw=148) followed immediately by 0.316 grams of JEFFAMINE® T-403 (0.72 mmoles, mw=440) directly through the condenser. Allow the reaction to reflux for 48 hours. Allow the reaction mixture to cool to room temperature. The reaction can sit until your next day in the lab. Estimate the purity and extent of the reaction by TLC on normal phase TLC with 98:2 ethanol:ammonium hydroxide as the solvent system. The product should be fluorescent when viewed under blue (450 nm) light.

Estimate the aqueous solubility by adding small aliquots of product to 10 ml of PBS with vigorous stirring. When the solution appears to be saturated and in equilibrium with solid product (or oil), continue to stir for 30 minutes. Then allow to settle for 30 minutes and then measure the absorbance at 440 nm. Make serial 1:10 dilutions in PBS if the measured absorbance is above 1.

Example 19—Proposed Reaction Scheme
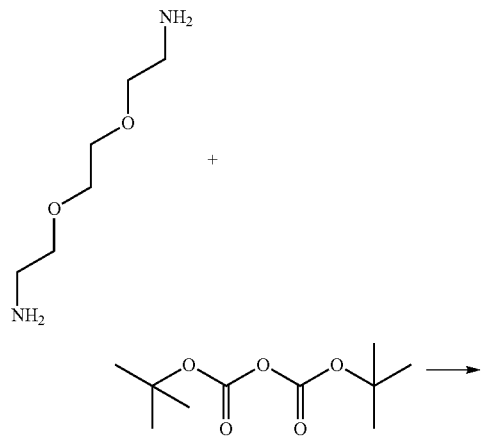
Jeffamine-Boc
Step 2—
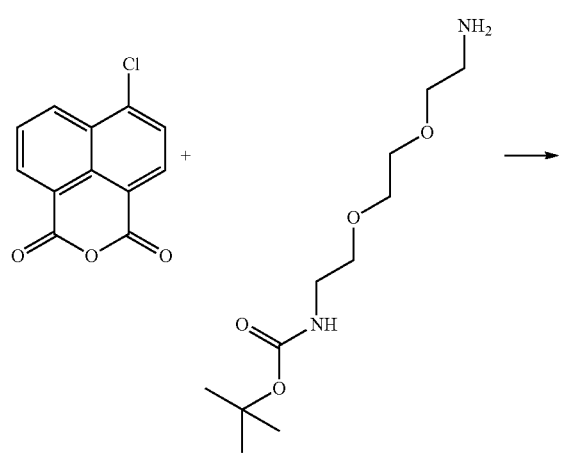
4-Cl
Step 3—
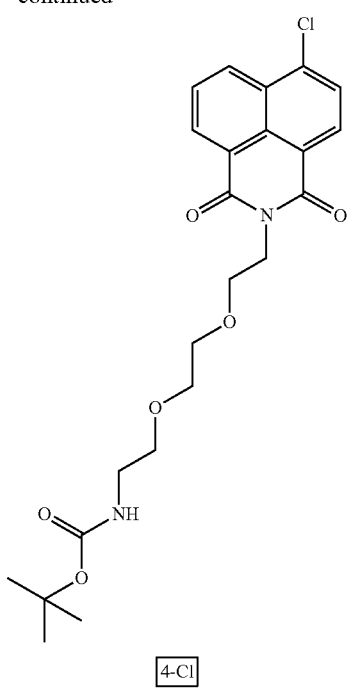
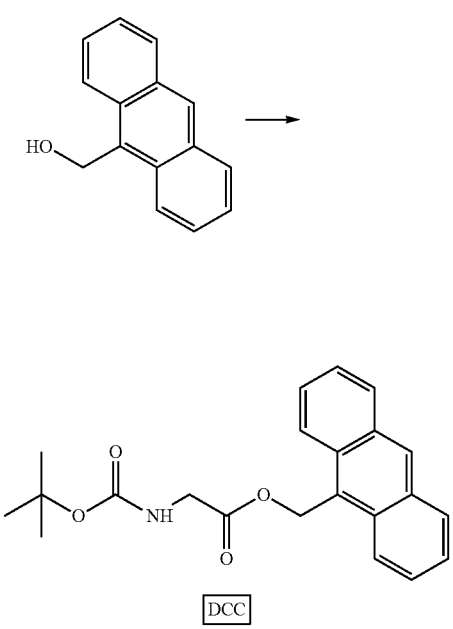
DCC Step 4—

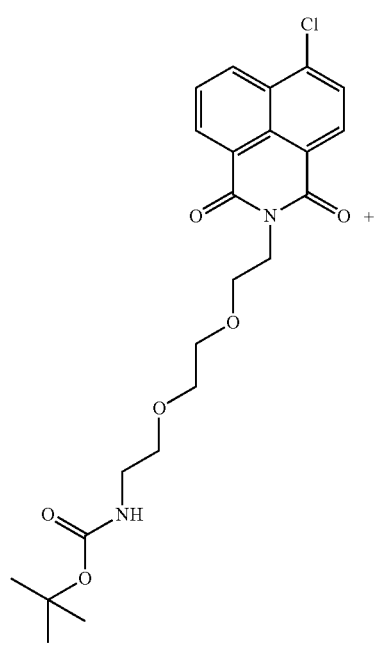

+

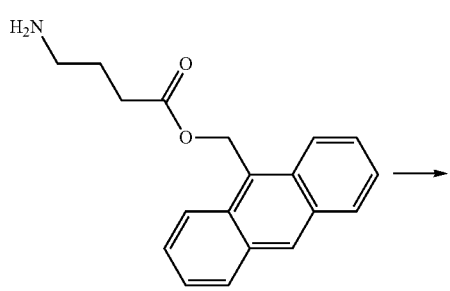

→

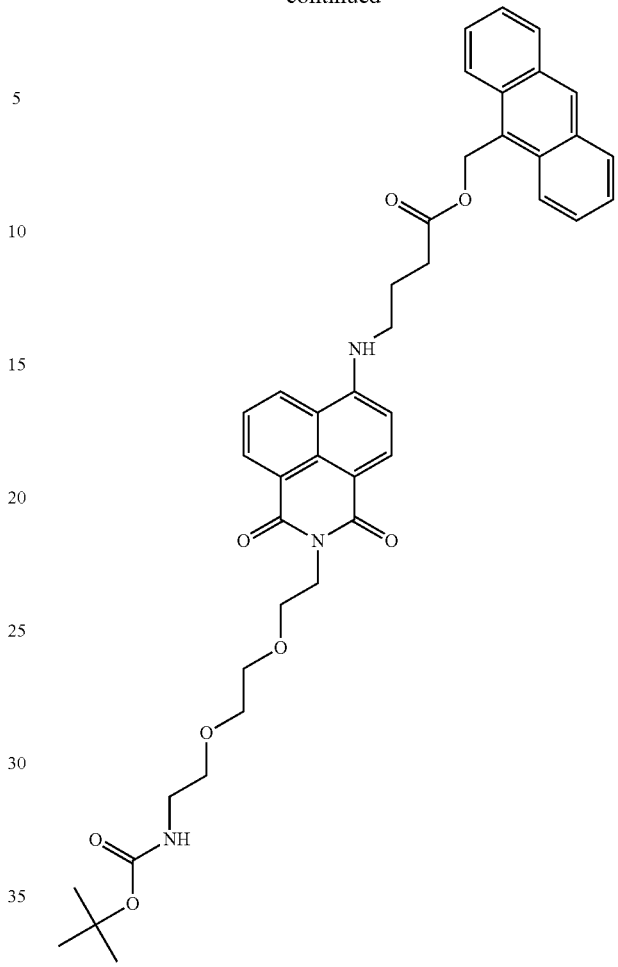

Example 20

Porcine internal carotid and femoral arteries (mixed breed and sex) were obtained from a local slaughterhouse (John Morrell, Sioux Falls, S. Dak.) on an as-needed basis. After excision, specimens were placed over ice and delivered to the laboratory within an hour of harvest. Arteries were rinsed with cold water to remove blood, cleaned using a scissors and forceps to remove adventitia and connective tissue, and then placed in a beaker of cold phosphate buffered saline (1×PBS, 8 g NaCl, 0.2 g KCl, 1.44 g $Na_2HPO_4$, 0.24 g $KH_2PO_4$ into one liter of dH2O, and pH adjusted to 7.4). They were then evaluated for usability (i.e., minimal vessel tapering and collaterals) and cut into approximately 4.5 cm sections. Arteries were then stored for a maximum of 12 hours at 4° C. in PBS until use that same day.

All experiments were conducted at room temperature. In each experiment, arteries were classified as Native, Untreated, or Treated. Native arteries received no additional treatment. These specimens were used to assess arterial quality prior to testing, or to study the native matrix. Untreated arteries received only balloon angioplasty (BA); Treated arteries received BA followed by photochemical treatment with a 4-amino-1,8-naphthalimide. Prior to BA, arteries were sized (luminal diameter) so that the correct angioplasty balloon size (Maveric, over the wire, Boston Scientific, Boston, Mass.; Buckling studies, Fox Plus, Abbott, Abbott Park, Ill.) could be chosen to achieve the desired overstretch of 25%. "Overstretch" was defined as the percent increase in luminal diameter that the angioplasty balloon imparted compared to the artery's native diameter. The native diameter was calculated by cutting off a small portion of the selected artery, cutting the vessel open, gently flattening it between two glass microscope slides, and then using a digital caliper to measure the circumference (as length) of the lumen. The luminal diameter was then calculated by dividing the circumference by Tr. The catheter used to apply BA was then selected by comparison of the calculated luminal diameter to manufacturer sizing charts provided with the BA catheter. When BA was performed on Untreated and Treated arteries, the catheter balloon was centered in the artery and the balloon was inflated using an indeflator (Guidant, St. Paul, Minn.) following the catheter manufacturer guidelines. The balloon was maintained at the maximum inflation for a period of 60 seconds and then deflated and removed from the artery. Arteries were irrigated with PBS during treatment to avoid dehydration, and then placed into PBS for 15-60 minutes prior to analysis.

After BA, the process for photochemically treating an ex vivo artery began by placing the vessel into a specially designed mounting apparatus and filling the lumen with the disclosed composition (2.5 mM). The disclosed composition was allowed to diffuse into the artery for a 5-minute period; then the catheter was inserted, centered in the BA treatment zone, and inflated (25% overstretch). With the balloon inflated, light from a monochromatic 457 nm laser (blue light 2 Watt, Laserglow, Toronto, ON; 457 nm; delivered at 450 Mw) was channeled through a custom light fiber to the treatment site for 60 seconds. After light activation, the balloon was immediately deflated and removed from the artery. Arteries were bathed with PBS during treatment to avoid dehydration and then placed into PBS after treatment to allow for relaxation and rehydration.

Measurement of Luminal Gain

After the artery had received the appropriate treatment, the luminal diameter was calculated from direct measurement of the cross-section (circumference) of the arterial lumen as follows: The artery was cut longitudinally and, using a digital caliper, three measurements of the cross-section were made in both the treated (n=6) and untreated (n=6-8) sections of artery. The three measurements were averaged and luminal diameter calculated as specified in the previous section. Luminal gain is defined as the percent increase from the pre-BA measurement as follows:

Increase in Luminal Diameter Post-BA(mm)−Luminal Diameter Pre-BA(mm)/Luminal Diameter Pre-BA(mm)×100.

Data were expressed as a mean±standard error (S.E.) for n number of ex vivo arteries. Unpaired Student's t test or multivariate analysis of variance was used for statistical analysis as appropriate.

Figure 14:
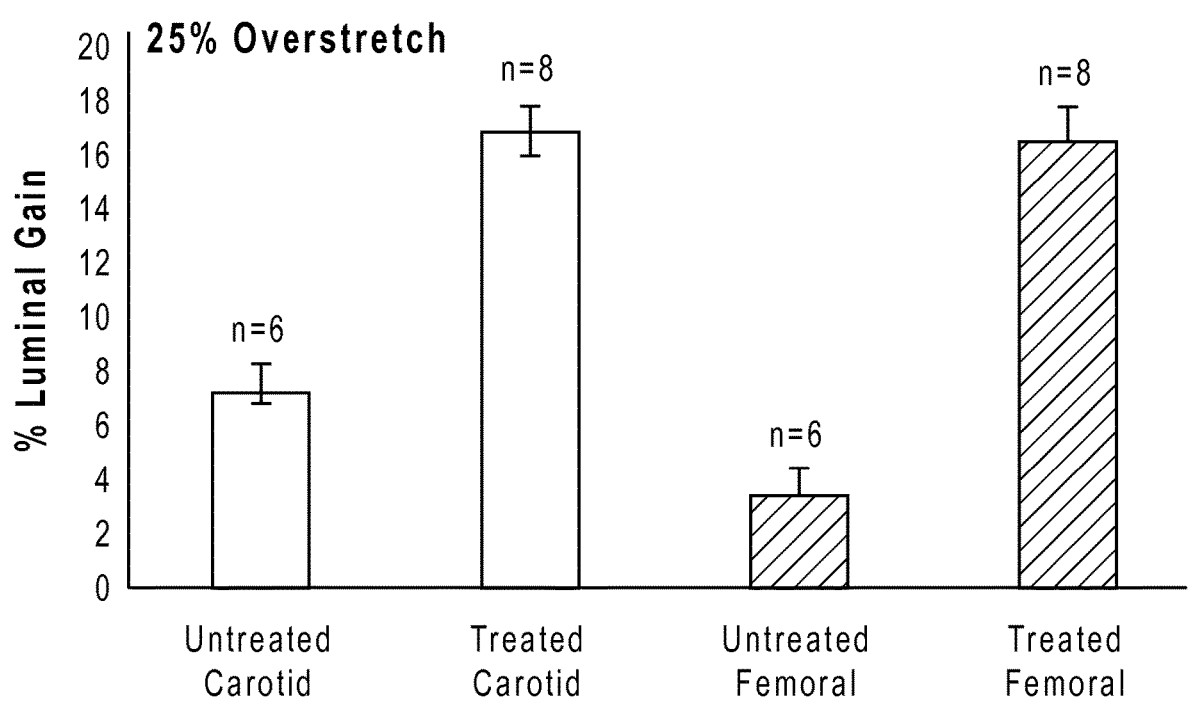
FIG. 14 is a graph illustrating the percent luminal gain in untreated and treated carotid porcine arteries and untreated and treated femoral porcine arteries.

FIG. 14 shows a plot of the data comparing luminal gain values for arteries receiving BA alone (Untreated) and BA plus photochemical treatment (Treated) with the disclosed composition comprising a 4-amino-1,8-naphthalimide. Treated arteries clearly demonstrated increased retention of luminal gain over untreated arteries (i.e., those receiving BA alone).

Measurement of Global Stretch Ratio, Distensibility, and Compliance Coeffecients The compliance and distensibility of the artery was analyzed by comparing the change in cross-sectional diameter (mm) as a function of hydrostatic pressure (mmHg) in the vessel. Native, Untreated, and Treated arteries were prepared as described above (n=6/group). Pressure was applied and monitored using a pressure transducer, and data collection software (DATAQ). At zero pressure, four artery diameter measurements were made using a digital caliper to the outside of the artery and marked with a permanent marker for subsequent measurements. For the Untreated and Treated arteries, these measurements were made central to the area receiving treatment with the angioplasty balloon. Immediately after taking zero pressure measurements, pressure in the vessel was increased to 50 mm Hg, and the same measurements were made after allowing 30 seconds for pressure equilibration. This process was repeated at pressures of 75, 100, 125, 150, and 200 mm Hg. During this process the outside of the suspended artery was kept hydrated by frequent washes with PBS.

A ratio termed the Global Stretch Ratio (GSR) was calculated by dividing the artery diameter (d) at a given pressure $d_P$, by the diameter at zero pressure $d_o$. Cross-sectional area is defined as $A=\pi r^2$, with $r=d/2$ (A, area; r, radius; d, diameter). Cross-sectional compliance coefficient is defined as $\Delta A/\Delta P$ (P=hydrostatic pressure). Distensibility coefficient is $(\Delta A/A)/\Delta P$.

Compliance values represent the slope of the Global Stretch Ratio (GSR) versus hydrostatic pressure curve. The slope of the curve was measured for data points at or above 125 mm Hg, which is the inflection point for where the curves differ after the 25% balloon stretch. Data were expressed as a mean±S.E. for n number of ex vivo arteries. Multivariate analysis of variance was used for statistical analysis.

Figure 15:
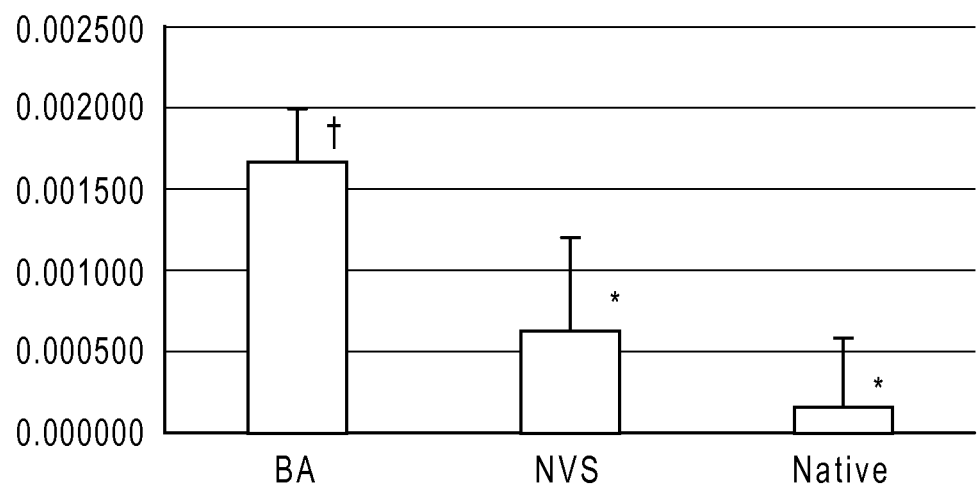
FIG. 15 is a graph illustrating the distensibility coefficient for Native, Untreated, and Treated arteries.
Figure 16:
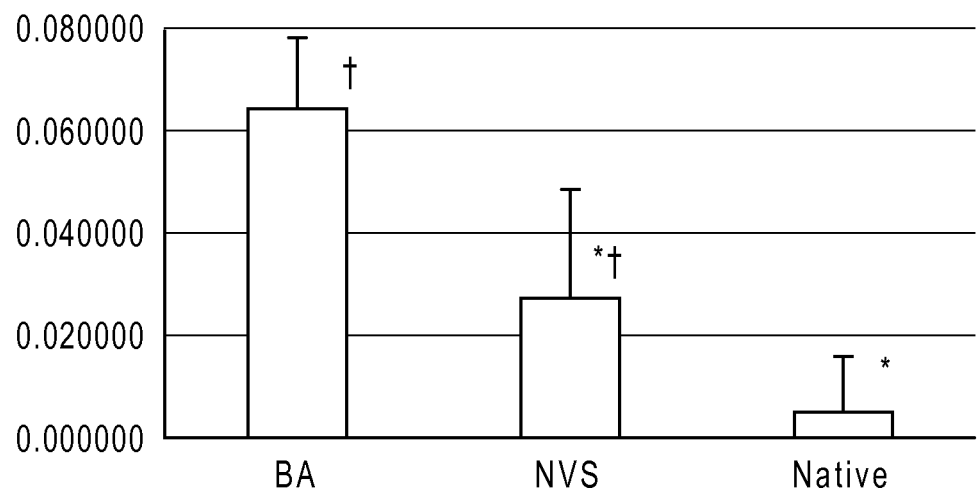
FIG. 16 is a graph illustrating the cross-sectional compliance for Native, Untreated, and Treated arteries.

Comparison of diameters for each pressure point revealed differences in the curves above 100-125 mmHg, for balloon stretched arteries. These curves then became quite different and this is reflected in the compliance and distensibility measurements. The diameters above 100 mmHg relate directly to the luminal gain imparted by the BA. Therefore, both Cross-sectional Compliance Coefficient and Cross-sectional Distensibilty was calculated from 125-200 mmHg and presented in FIGS. 15 and 16. The differences between all three treatment groups are statistically significant (p<0.0001). Most importantly, the Treated arteries (FIGS. 15 and 16 "NVS") are different, which reflected a smaller slope and more non-compliant behavior than the Untreated arteries (FIGS. 15 and 16 "BA"). Because the Treated artery also received BA prior to photoactivation, the change in GSR compliance value provided compelling evidence that the disclosed method restored vessel compliance in comparison to that of the native blood vessel.

Measurement of Buckling

Figure 17:
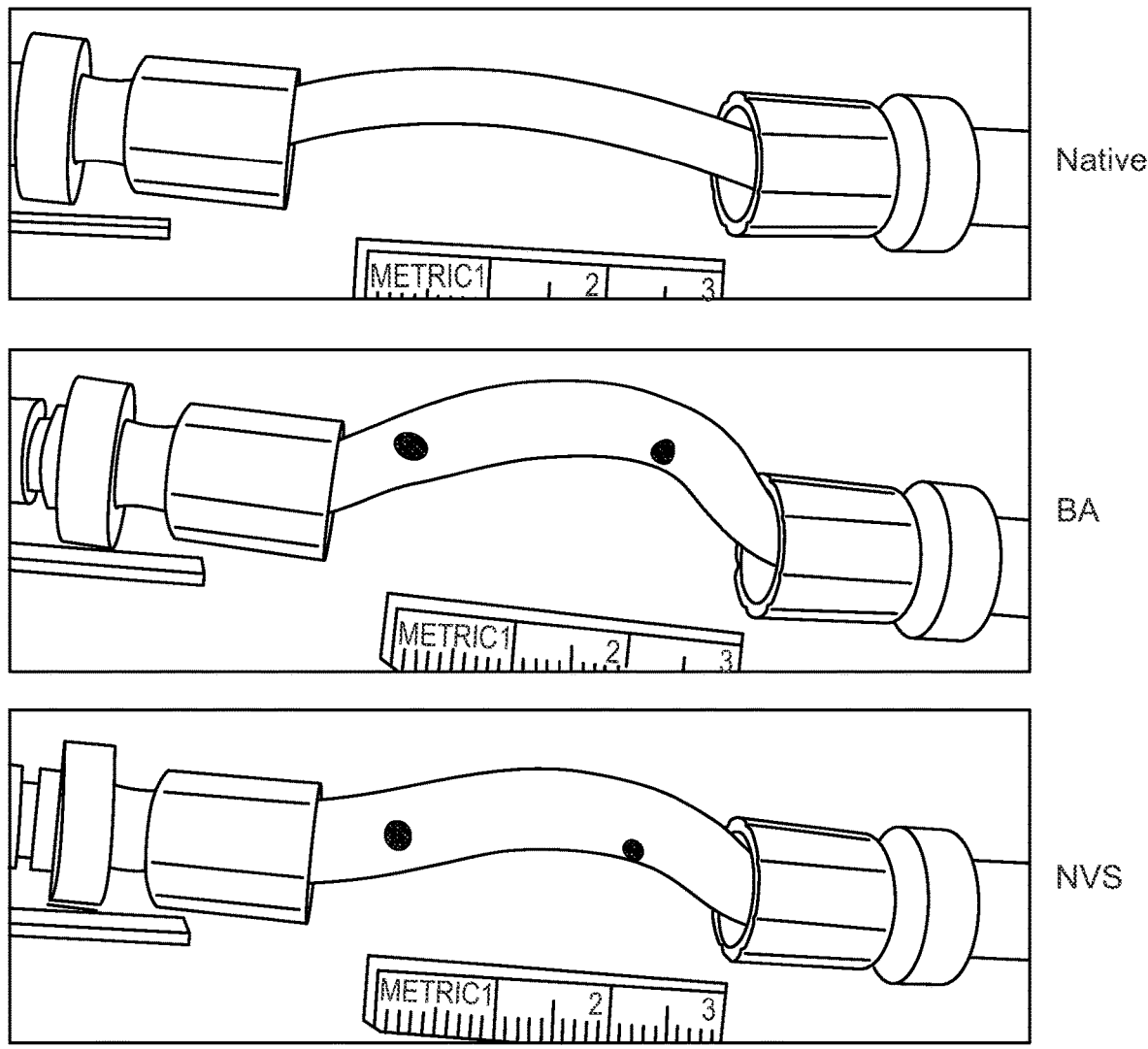
FIG. 17 is a photo illustrating the buckling of various blood vessels at 200 mmHg of pressure.
Figure 18:
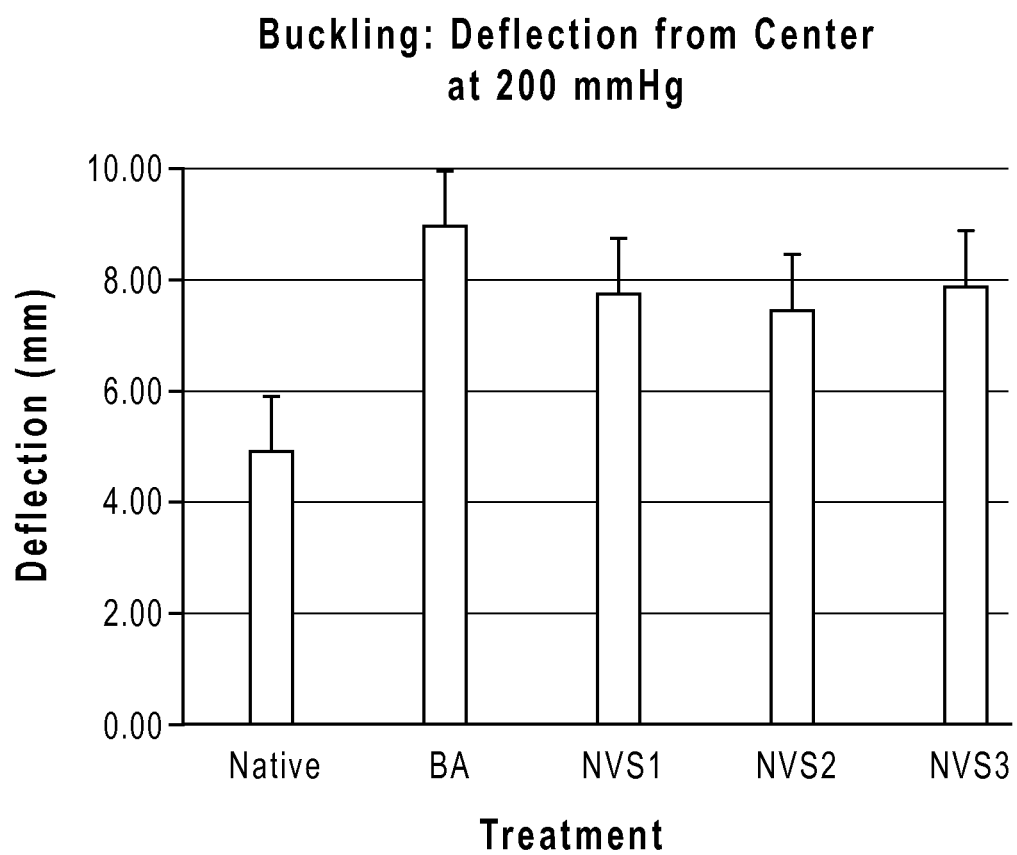
FIG. 18 is a graph illustrating the buckling of various native, untreated, and treated blood vessels.

After the artery was measured for length and balloon size, it was suspended in PBS and secured at a 30% axial stretch and subjected to increasing internal hydraulic pressures. The artery was initially pressurized to 200 mmHg and then released to zero. Then the artery was inflated from 0 to 100, 150, and then 200 mmHg. Lateral displacement and exterior diameter were measured from photos taken in Native arteries. Buckling was generally only observed after 200 mmHg in healthy, Native arteries. If a Native artery demonstrated any buckling at 100-150 mmHg, it was discarded and not included in the analysis. Then the artery was over-stretched to 25% by BA as described above and then pressurized to 150 and 200 mmHg. Photos were taken at both pressures. Then the artery was treated with the disclosed composition and light activated as described above. The artery was then inflated to 150 and 200 mmHg for a total of three times (NVS1, NVS2, NVS3) and photos were taken again at both 150 and 200 mmHg. Therefore, each artery was subjected to arterial pressures that caused buckling at Native, then BA (Untreated), and then NVS (Treated) conditions for a total of 6 inflations to 200 mmHg for every artery. Photos were taken at a perpendicular angle to the buckle. See FIG. 17. If the artery buckled in a different direction to the camera, the camera was repositioned in order to take the best photos of the maximum buckling of that artery. The central lines of the arteries were determined by calculating the center of the artery at each end of the artery near the coupling and then drawing a straight line between these two central coordinates. Then the displacement ("buckling") of the artery from the central line was measured at its maximal distance in the middle of the artery. A ruler was placed by each artery for photo comparison and the displacement was given as millimeters from the center line of the artery. Occasionally a kinked or twisted appearance was observed but only arteries that showed a simple curved buckle were used in the analysis.

The native artery began to show buckling behavior at 200 mmHg and BA caused this buckling to increase significantly (from 4.9±2.2 to 9.0±2.0 mm, P<0.002, vs BA). After treatment with the disclosed composition and light activation, the buckling was reduced by about 15% in each artery and subsequent buckling remained stable at that reduced value (to 7.8, 7.7, and 7.9, NVS1, NVS2, NVS3, respectively, p<0.02 vs BA). Arteries that were damaged by 25% overstretch with BA were partially repaired with the disclosed process as evident by reduced buckling in the artery.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of restoring vascular compliance in a diseased blood vessel, comprising:
    inserting a delivery system into the blood vessel;
    applying a bolus of a composition comprising a 4-amino-1,8-naphthalimide compound to the blood vessel; and
    activating the composition with a sufficient amount of electromagnetic energy to restore the vascular compliance of the blood vessel; wherein the 4-amino-1,8-naphthalimide compound comprises

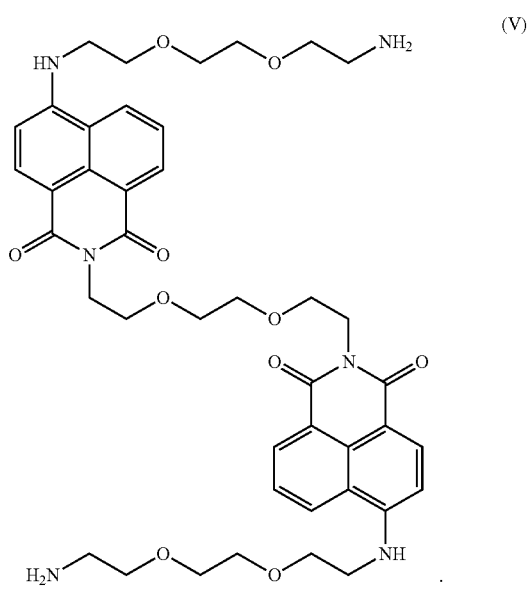 [SMILES: NCCOCCOCCNc1ccc2c3c(cccc13)C(=O)N(CCOCCOCCN1C(=O)c3cccc4c(NCCOCCOCCN)ccc(c34)C1=O)C2=O]

2. The method of claim 1, wherein the blood vessel is an artery or a vein.

3. The method of claim 1, wherein the vascular compliance of the blood vessel is restored to its native compliance within seconds to about 120 days after the activating step.

4. The method of claim 1, wherein the composition further comprises one or more excipients, buffers, carriers, stabilizers, preservatives, solvents and/or bulking agents.

5. The method of claim 4, wherein the composition further comprises a solvent.

6. The method of claim 5, wherein the solvent is phosphate buffered saline.

7. The method of claim 5, wherein the solvent comprises dimethylformamide or isopropyl alcohol.

8. The method of claim 5, wherein the 1,4-amino-8-napthalimide compound is present in a concentration from about 0.01 mg/mL to about 100 mg/mL.

9. The method of claim 5, wherein the 1,4-amino-8-napthalimide compound is present in a concentration from about 0.1 mg/mL to about 50 mg/mL.

10. The method of claim 5, wherein the 1,4-amino-8-napthalimide compound is present in a concentration from about 1 mg/mL to about 30 mg/mL.

11. The method of claim 1, wherein the electromagnetic energy comprises blue light.

12. The method of claim 1, wherein the composition further comprises acetate ions.

13. The method of claim 6, wherein the composition further comprises acetate ions.

14. The method of claim 7, wherein the composition further comprises acetate ions.

* * * * *